US012569252B2

(12) United States Patent
Li et al.

(10) Patent No.: US 12,569,252 B2
(45) **Date of Patent: *Mar. 10, 2026**

(54) SYSTEMS AND METHODS FOR TREATING ANEURYSMS

(71) Applicant: Covidien LP, Mansfield, MA (US)

(72) Inventors: Junwei Li, Irvine, CA (US); Mark Ashby, Laguna Niguel, CA (US); Hoai Nguyen, Westminster, CA (US)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/505,645

(22) Filed: Nov. 9, 2023

(65) Prior Publication Data

US 2024/0075565 A1     Mar. 7, 2024

Related U.S. Application Data

(63) Continuation of application No. 16/949,561, filed on Nov. 3, 2020, now Pat. No. 11,826,863.
(Continued)

(51) Int. Cl.
*A61B 17/12* (2006.01)
*A61B 17/00* (2006.01)
(Continued)

(52) U.S. Cl.
CPC .. *A61B 17/12113* (2013.01); *A61B 17/12031* (2013.01); *A61B 17/1214* (2013.01);
(Continued)

(58) Field of Classification Search
CPC ........ A61B 17/12113; A61B 17/12118; A61B 17/12109; A61B 17/12172;
(Continued)

(56) References Cited

U.S. PATENT DOCUMENTS

| 5,041,090 A | 8/1991 | Scheglov et al. |
| 5,250,071 A | 10/1993 | Palermo |

(Continued)

FOREIGN PATENT DOCUMENTS

| CA | 2167911 A1 | 1/1996 |
| CA | 3031482 A1 | 8/2017 |

(Continued)

OTHER PUBLICATIONS

Material Spotlight Teflon for Electrical Insulation, Oct. 26, 2021, ESPE Manufacturing, p. 2 (Year: 2021).
(Continued)

*Primary Examiner* — Katherine H Schwiker
(74) *Attorney, Agent, or Firm* — Fortem IP LLP

(57) ABSTRACT

Treatment of aneurysms can be improved by delivering an occlusive member (e.g., an expandable braid) to an aneurysm sac in conjunction with an embolic element (e.g., coils, embolic material). A treatment system for such treatment can include an electrolytically corrodible core wire having a proximal portion, a distal portion, and a detachment zone between the proximal portion and the distal portion. An occlusive member having a proximal hub is coupled to the core wire distal portion. A conduit extends along at least a portion of the core wire. The conduit has a lumen configured to pass an embolic element therethrough.

20 Claims, 11 Drawing Sheets

Related U.S. Application Data

(60) Provisional application No. 62/930,303, filed on Nov. 4, 2019, provisional application No. 62/930,357, filed on Nov. 4, 2019, provisional application No. 62/930,487, filed on Nov. 4, 2019, provisional application No. 62/930,333, filed on Nov. 4, 2019, provisional application No. 62/930,421, filed on Nov. 4, 2019, provisional application No. 62/930,324, filed on Nov. 4, 2019.

(51) Int. Cl.
*A61B 90/00* (2016.01)
*B23P 19/04* (2006.01)

(52) U.S. Cl.
CPC .. *A61B 17/12145* (2013.01); *A61B 17/12172* (2013.01); *A61B 17/12186* (2013.01); *A61B 2017/00526* (2013.01); *A61B 2017/00557* (2013.01); *A61B 2017/00862* (2013.01); *A61B 2017/00929* (2013.01); *A61B 2017/12054* (2013.01); *A61B 2017/12063* (2013.01); *A61B 17/12168* (2013.01); *A61B 2090/376* (2016.02); *A61B 2090/3966* (2016.02); *B23P 19/047* (2013.01)

(58) Field of Classification Search
CPC ........ A61B 17/12022; A61B 17/12145; A61B 2017/1205; A61B 2017/12063
See application file for complete search history.

(56) References Cited

U.S. PATENT DOCUMENTS

| | | | |
|---|---|---|---|
| 5,261,916 A | 11/1993 | Engelson |
| 5,284,488 A | 2/1994 | Sideris |
| 5,326,350 A | 7/1994 | Li |
| 5,354,295 A | 10/1994 | Guglielmi et al. |
| 5,405,379 A | 4/1995 | Lane |
| 5,417,708 A | 5/1995 | Hall et al. |
| 5,601,600 A | 2/1997 | Ton |
| 5,645,558 A | 7/1997 | Horton |
| 5,669,931 A | 9/1997 | Kupiecki et al. |
| 5,725,552 A | 3/1998 | Kotula et al. |
| 5,733,294 A | 3/1998 | Forber et al. |
| 5,741,333 A | 4/1998 | Frid |
| 5,749,891 A | 5/1998 | Ken et al. |
| 5,749,894 A | 5/1998 | Engelson |
| 5,749,895 A | 5/1998 | Sawyer et al. |
| 5,749,919 A | 5/1998 | Blanc |
| 5,814,062 A | 9/1998 | Sepetka et al. |
| 5,823,198 A | 10/1998 | Jones et al. |
| 5,846,261 A | 12/1998 | Kotula et al. |
| 5,911,731 A | 6/1999 | Pham et al. |
| 5,916,235 A | 6/1999 | Guglielmi |
| 5,925,060 A | 7/1999 | Forber |
| 5,928,260 A | 7/1999 | Chin et al. |
| 5,935,148 A | 8/1999 | Villar et al. |
| 5,941,249 A | 8/1999 | Maynard |
| 5,944,730 A | 8/1999 | Nobles et al. |
| 5,944,738 A | 8/1999 | Amplatz et al. |
| 5,951,599 A | 9/1999 | McCrory |
| 5,964,797 A | 10/1999 | Ho |
| 5,976,169 A | 11/1999 | Imran |
| 5,980,554 A | 11/1999 | Lenker et al. |
| 6,022,374 A | 2/2000 | Imran |
| 6,033,423 A | 3/2000 | Ken et al. |
| 6,036,720 A | 3/2000 | Abrams et al. |
| 6,063,070 A | 5/2000 | Eder |
| 6,063,104 A | 5/2000 | Villar et al. |
| 6,077,260 A | 6/2000 | Wheelock et al. |
| 6,086,577 A | 7/2000 | Ken et al. |
| 6,090,125 A | 7/2000 | Horton |
| 6,093,199 A | 7/2000 | Brown et al. |
| 6,096,021 A | 8/2000 | Helm et al. |
| 6,123,715 A | 9/2000 | Amplatz |
| 6,139,564 A | 10/2000 | Teoh |
| 6,152,144 A | 11/2000 | Lesh et al. |
| 6,159,531 A | 12/2000 | Dang et al. |
| 6,165,193 A | 12/2000 | Greene et al. |
| 6,168,615 B1 | 1/2001 | Ken et al. |
| 6,168,622 B1 | 1/2001 | Mazzocchi |
| 6,238,403 B1 | 5/2001 | Greene et al. |
| 6,299,619 B1 | 10/2001 | Greene et al. |
| 6,309,367 B1 | 10/2001 | Boock |
| 6,322,576 B1 | 11/2001 | Wallace et al. |
| 6,344,048 B1 | 2/2002 | Chin et al. |
| 6,346,117 B1 | 2/2002 | Greenhalgh |
| 6,350,270 B1 | 2/2002 | Roue |
| 6,368,339 B1 | 4/2002 | Amplatz |
| 6,371,980 B1 | 4/2002 | Rudakov et al. |
| 6,375,668 B1 | 4/2002 | Gifford et al. |
| 6,379,329 B1 | 4/2002 | Naglreiter et al. |
| 6,383,174 B1 | 5/2002 | Eder |
| 6,391,037 B1 | 5/2002 | Greenhalgh |
| 6,428,558 B1 | 8/2002 | Jones et al. |
| 6,447,531 B1 | 9/2002 | Amplatz |
| 6,451,050 B1 | 9/2002 | Rudakov et al. |
| 6,454,780 B1 | 9/2002 | Wallace |
| 6,494,884 B2 | 12/2002 | Gifford et al. |
| 6,506,204 B2 | 1/2003 | Mazzocchi |
| 6,511,468 B1 | 1/2003 | Cragg et al. |
| 6,547,804 B2 | 4/2003 | Porter et al. |
| 6,551,303 B1 | 4/2003 | Van et al. |
| 6,569,179 B2 | 5/2003 | Teoh et al. |
| 6,579,303 B2 | 6/2003 | Amplatz |
| 6,585,748 B1 | 7/2003 | Jeffree |
| 6,589,256 B2 | 7/2003 | Forber |
| 6,589,265 B1 | 7/2003 | Palmer et al. |
| 6,591,472 B1 | 7/2003 | Noone et al. |
| 6,592,605 B2 | 7/2003 | Lenker et al. |
| 6,599,308 B2 | 7/2003 | Amplatz |
| 6,602,261 B2 | 8/2003 | Greene et al. |
| 6,605,101 B1 | 8/2003 | Schaefer et al. |
| 6,605,102 B1 | 8/2003 | Mazzocchi et al. |
| 6,605,111 B2 | 8/2003 | Bose et al. |
| 6,613,074 B1 | 9/2003 | Mitelberg et al. |
| 6,626,939 B1 | 9/2003 | Burnside et al. |
| 6,635,068 B1 | 10/2003 | Dubrul et al. |
| 6,652,555 B1 | 11/2003 | VanTassel et al. |
| 6,652,556 B1 | 11/2003 | VanTassel et al. |
| 6,666,882 B1 | 12/2003 | Bose et al. |
| 6,669,717 B2 | 12/2003 | Marotta et al. |
| 6,669,721 B1 | 12/2003 | Bose et al. |
| 6,682,546 B2 | 1/2004 | Amplatz |
| 6,689,150 B1 | 2/2004 | VanTassel et al. |
| 6,689,486 B2 | 2/2004 | Ho et al. |
| 6,723,112 B2 | 4/2004 | Ho et al. |
| 6,723,116 B2 | 4/2004 | Taheri |
| 6,730,108 B2 | 5/2004 | Van et al. |
| 6,746,468 B1 | 6/2004 | Sepetka et al. |
| 6,746,890 B2 | 6/2004 | Gupta et al. |
| 6,780,196 B2 | 8/2004 | Chin et al. |
| 6,802,851 B2 | 10/2004 | Jones et al. |
| 6,811,560 B2 | 11/2004 | Jones et al. |
| 6,855,153 B2 | 2/2005 | Saadat |
| 6,855,154 B2 | 2/2005 | Abdel-Gawwad |
| 6,878,384 B2 | 4/2005 | Cruise et al. |
| 6,905,503 B2 | 6/2005 | Gifford et al. |
| 6,936,055 B1 | 8/2005 | Ken et al. |
| 6,936,058 B2 | 8/2005 | Forde et al. |
| 6,949,113 B2 | 9/2005 | Van et al. |
| 6,953,473 B2 | 10/2005 | Porter |
| 6,989,019 B2 | 1/2006 | Mazzocchi et al. |
| 6,991,617 B2 | 1/2006 | Hektner et al. |
| 6,994,092 B2 | 2/2006 | Van et al. |
| 6,994,717 B2 | 2/2006 | Konya et al. |
| 7,011,671 B2 | 3/2006 | Welch |
| 7,014,645 B2 | 3/2006 | Greene et al. |
| 7,029,487 B2 | 4/2006 | Greene et al. |
| 7,029,949 B2 | 4/2006 | Farnworth et al. |
| 7,070,609 B2 | 7/2006 | West |
| 7,083,632 B2 | 8/2006 | Avellanet et al. |

(56)                References Cited

U.S. PATENT DOCUMENTS

| | | |
|---|---|---|
| 7,098,194 B2 | 8/2006 | Chenite et al. |
| 7,128,073 B1 | 10/2006 | Van et al. |
| 7,128,736 B1 | 10/2006 | Abrams et al. |
| 7,153,323 B1 | 12/2006 | Teoh et al. |
| 7,169,177 B2 | 1/2007 | Obara |
| 7,195,636 B2 | 3/2007 | Avellanet et al. |
| 7,229,461 B2 | 6/2007 | Chin et al. |
| 7,232,461 B2 | 6/2007 | Ramer |
| 7,306,622 B2 | 12/2007 | Jones et al. |
| 7,326,225 B2 | 2/2008 | Ferrera et al. |
| 7,331,980 B2 | 2/2008 | Dubrul et al. |
| 7,367,986 B2 | 5/2008 | Mazzocchi et al. |
| 7,410,482 B2 | 8/2008 | Murphy et al. |
| 7,419,503 B2 | 9/2008 | Pulnev et al. |
| 7,473,266 B2 | 1/2009 | Glaser |
| 7,481,821 B2 | 1/2009 | Fogarty et al. |
| 7,491,214 B2 | 2/2009 | Greene et al. |
| 7,569,066 B2 | 8/2009 | Gerberding et al. |
| 7,572,288 B2 | 8/2009 | Cox |
| 7,597,704 B2 | 10/2009 | Frazier et al. |
| 7,601,160 B2 | 10/2009 | Richter |
| 7,608,088 B2 | 10/2009 | Jones et al. |
| 7,695,488 B2 | 4/2010 | Berenstein et al. |
| 7,699,056 B2 | 4/2010 | Tran et al. |
| 7,708,754 B2 | 5/2010 | Balgobin et al. |
| 7,727,189 B2 | 6/2010 | VanTassel et al. |
| 7,744,583 B2 | 6/2010 | Seifert et al. |
| 7,744,652 B2 | 6/2010 | Morsi |
| 7,879,065 B2 | 2/2011 | Gesswein et al. |
| 7,976,527 B2 | 7/2011 | Cragg et al. |
| RE42,625 E | 8/2011 | Guglielmi |
| 7,993,364 B2 | 8/2011 | Morsi |
| RE42,758 E | 9/2011 | Ken et al. |
| 8,012,210 B2 | 9/2011 | Lin et al. |
| 8,043,326 B2 | 10/2011 | Hancock et al. |
| 8,062,379 B2 | 11/2011 | Morsi |
| 8,075,585 B2 | 12/2011 | Lee et al. |
| 8,137,293 B2 | 3/2012 | Zhou et al. |
| 8,142,456 B2 | 3/2012 | Rosqueta et al. |
| 8,153,612 B2 | 4/2012 | Ben-Shalom et al. |
| 8,202,280 B2 | 6/2012 | Richter |
| 8,211,160 B2 | 7/2012 | Garrison et al. |
| 8,221,445 B2 | 7/2012 | Van et al. |
| 8,333,783 B2 | 12/2012 | Braun et al. |
| 8,343,167 B2 | 1/2013 | Henson |
| 8,361,104 B2 | 1/2013 | Jones et al. |
| 8,361,138 B2 | 1/2013 | Adams |
| 8,372,062 B2 | 2/2013 | Murphy et al. |
| 8,398,670 B2 | 3/2013 | Amplatz et al. |
| 8,425,541 B2 | 4/2013 | Masters et al. |
| 8,470,013 B2 | 6/2013 | Duggal et al. |
| 8,530,632 B2 | 9/2013 | Tijsma et al. |
| 8,597,320 B2 | 12/2013 | Sepetka et al. |
| 8,603,128 B2 | 12/2013 | Greene et al. |
| 8,653,319 B2 | 2/2014 | Amery et al. |
| 8,690,936 B2 | 4/2014 | Nguyen et al. |
| 8,715,317 B1 | 5/2014 | Janardhan et al. |
| 8,809,301 B2 | 8/2014 | Athanasiadis et al. |
| 8,834,515 B2 | 9/2014 | Win et al. |
| 8,840,867 B2 | 9/2014 | Sophie et al. |
| 8,906,057 B2 | 12/2014 | Connor et al. |
| 8,974,512 B2 | 3/2015 | Aboytes et al. |
| 8,998,947 B2 | 4/2015 | Aboytes et al. |
| 9,034,348 B2 | 5/2015 | Ben-Shalom et al. |
| 9,192,574 B2 | 11/2015 | Medina et al. |
| 9,192,692 B2 | 11/2015 | Medina et al. |
| 9,211,202 B2 | 12/2015 | Strother et al. |
| 9,301,769 B2 | 4/2016 | Brady et al. |
| 9,314,248 B2 | 4/2016 | Molaei |
| 9,333,220 B2 | 5/2016 | Tijsma et al. |
| 9,339,275 B2 | 5/2016 | Trommeter et al. |
| 9,433,636 B2 | 9/2016 | Tijsma et al. |
| 9,486,224 B2 | 11/2016 | Riina et al. |
| 9,555,120 B2 | 1/2017 | Andersson |
| 9,629,636 B2 | 4/2017 | Fogarty et al. |
| 9,655,842 B1 | 5/2017 | Girdhar et al. |
| 9,681,861 B2 | 6/2017 | Heisel et al. |
| 9,700,648 B2 | 7/2017 | Hissong et al. |
| 9,713,475 B2 | 7/2017 | Divino et al. |
| 9,731,043 B2 | 8/2017 | Lerouge et al. |
| 9,833,309 B2 | 12/2017 | Levi et al. |
| 9,844,380 B2 | 12/2017 | Furey |
| 9,901,543 B2 | 2/2018 | Chausson et al. |
| 9,907,684 B2 | 3/2018 | Connor et al. |
| 9,918,718 B2 | 3/2018 | Lorenzo |
| 9,925,210 B2 | 3/2018 | Mccarthy et al. |
| 9,962,146 B2 | 5/2018 | Hebert et al. |
| 10,028,745 B2 | 7/2018 | Morsi |
| 10,130,372 B2 | 11/2018 | Griffin |
| 10,517,986 B2 | 12/2019 | Sherman et al. |
| 10,576,099 B2 | 3/2020 | Li et al. |
| 10,632,143 B2 | 4/2020 | Mccarthy et al. |
| 10,932,933 B2 | 3/2021 | Bardsley et al. |
| 10,952,740 B2 | 3/2021 | Dasnurkar et al. |
| 11,076,860 B2 | 8/2021 | Lorenzo |
| 11,134,953 B2 | 10/2021 | Solaun |
| 11,179,159 B2 | 11/2021 | Cox et al. |
| 11,389,309 B2 | 7/2022 | Ruvalcaba et al. |
| 11,504,816 B2 | 11/2022 | Nguyen et al. |
| 11,679,458 B2 | 6/2023 | Nguyen et al. |
| 11,685,007 B2 | 6/2023 | Li et al. |
| 11,690,628 B2 | 7/2023 | Divino et al. |
| 11,717,924 B2 | 8/2023 | Nguyen et al. |
| 11,786,253 B2 | 10/2023 | Divino et al. |
| 11,826,863 B2 | 11/2023 | Li et al. |
| 12,251,110 B2 | 3/2025 | Nguyen et al. |
| 12,256,936 B2 | 3/2025 | Li et al. |
| 12,295,582 B2 | 5/2025 | Nguyen et al. |
| 2001/0000797 A1 | 5/2001 | Mazzocchi |
| 2001/0001835 A1 | 5/2001 | Greene et al. |
| 2002/0026210 A1 | 2/2002 | Abdel-Gawwad |
| 2002/0042628 A1 | 4/2002 | Chin et al. |
| 2002/0062145 A1 | 5/2002 | Rudakov et al. |
| 2002/0119177 A1 | 8/2002 | Bowman et al. |
| 2002/0147462 A1 | 10/2002 | Mair et al. |
| 2002/0165572 A1 | 11/2002 | Saadat |
| 2002/0169473 A1 | 11/2002 | Sepetka et al. |
| 2002/0193812 A1 | 12/2002 | Patel et al. |
| 2002/0193813 A1 | 12/2002 | Helkowski et al. |
| 2003/0004533 A1 | 1/2003 | Dieck et al. |
| 2003/0004568 A1 | 1/2003 | Ken et al. |
| 2003/0018294 A1 | 1/2003 | Cox |
| 2003/0028209 A1 | 2/2003 | Teoh et al. |
| 2003/0040772 A1 | 2/2003 | Hyodoh et al. |
| 2003/0055440 A1 | 3/2003 | Jones et al. |
| 2003/0065303 A1 | 4/2003 | Wellman et al. |
| 2003/0093097 A1* | 5/2003 | Avellanet ........... A61B 17/1219 606/157 |
| 2003/0093111 A1 | 5/2003 | Ken et al. |
| 2003/0113478 A1 | 6/2003 | Dang et al. |
| 2003/0114918 A1 | 6/2003 | Garrison et al. |
| 2003/0149490 A1 | 8/2003 | Ashman |
| 2003/0171739 A1 | 9/2003 | Murphy et al. |
| 2003/0187473 A1 | 10/2003 | Berenstein et al. |
| 2003/0195553 A1 | 10/2003 | Wallace et al. |
| 2003/0212419 A1 | 11/2003 | West |
| 2004/0034386 A1 | 2/2004 | Fulton et al. |
| 2004/0044361 A1 | 3/2004 | Frazier et al. |
| 2004/0044391 A1 | 3/2004 | Porter |
| 2004/0064093 A1 | 4/2004 | Hektner et al. |
| 2004/0098027 A1 | 5/2004 | Teoh et al. |
| 2004/0106945 A1 | 6/2004 | Thramann et al. |
| 2004/0115164 A1 | 6/2004 | Pierce et al. |
| 2004/0122467 A1 | 6/2004 | VanTassel et al. |
| 2004/0133222 A1 | 7/2004 | Tran et al. |
| 2004/0138758 A1 | 7/2004 | Kronengold et al. |
| 2004/0161451 A1 | 8/2004 | Pierce et al. |
| 2004/0167597 A1 | 8/2004 | Costantino et al. |
| 2004/0176798 A1 | 9/2004 | Foy et al. |
| 2004/0181253 A1 | 9/2004 | Sepetka et al. |
| 2004/0236344 A1 | 11/2004 | Monstadt et al. |
| 2005/0021077 A1 | 1/2005 | Chin et al. |
| 2005/0038470 A1 | 2/2005 | Van et al. |
| 2005/0049625 A1 | 3/2005 | Shaya et al. |

(56)     References Cited

U.S. PATENT DOCUMENTS

| | | |
|---|---|---|
| 2005/0119684 A1 | 6/2005 | Guterman et al. |
| 2005/0131443 A1 | 6/2005 | Abdel-Gawwad |
| 2005/0222580 A1 | 10/2005 | Gifford et al. |
| 2005/0267510 A1 | 12/2005 | Razack |
| 2005/0267511 A1 | 12/2005 | Marks et al. |
| 2005/0267527 A1 | 12/2005 | Sandoval et al. |
| 2005/0277978 A1 | 12/2005 | Greenhalgh |
| 2005/0278023 A1 | 12/2005 | Zwirkoski |
| 2006/0028209 A1 | 2/2006 | Walker |
| 2006/0034883 A1 | 2/2006 | Dang et al. |
| 2006/0052816 A1 | 3/2006 | Bates et al. |
| 2006/0064151 A1 | 3/2006 | Guterman et al. |
| 2006/0106421 A1 | 5/2006 | Teoh |
| 2006/0116709 A1 | 6/2006 | Sepetka et al. |
| 2006/0116712 A1 | 6/2006 | Sepetka et al. |
| 2006/0116713 A1 | 6/2006 | Sepetka et al. |
| 2006/0116714 A1 | 6/2006 | Sepetka et al. |
| 2006/0122548 A1 | 6/2006 | Abrams |
| 2006/0155323 A1 | 7/2006 | Porter et al. |
| 2006/0190070 A1 | 8/2006 | Dieck et al. |
| 2006/0200234 A1 | 9/2006 | Hines |
| 2006/0206140 A1 | 9/2006 | Shaolian et al. |
| 2006/0206198 A1 | 9/2006 | Churchwell et al. |
| 2006/0206199 A1 | 9/2006 | Churchwell et al. |
| 2006/0241686 A1 | 10/2006 | Ferrera et al. |
| 2006/0247680 A1 | 11/2006 | Amplatz et al. |
| 2006/0271162 A1 | 11/2006 | Vito et al. |
| 2006/0276824 A1 | 12/2006 | Mitelberg et al. |
| 2006/0276829 A1 | 12/2006 | Balgobin et al. |
| 2006/0276830 A1 | 12/2006 | Balgobin et al. |
| 2007/0003594 A1 | 1/2007 | Brady et al. |
| 2007/0010850 A1 | 1/2007 | Balgobin et al. |
| 2007/0014831 A1 | 1/2007 | Sung et al. |
| 2007/0083226 A1 | 4/2007 | Buiser et al. |
| 2007/0100426 A1 | 5/2007 | Rudakov et al. |
| 2007/0135907 A1 | 6/2007 | Wilson et al. |
| 2007/0167876 A1 | 7/2007 | Euteneuer et al. |
| 2007/0167877 A1 | 7/2007 | Euteneuer et al. |
| 2007/0167972 A1 | 7/2007 | Euteneuer et al. |
| 2007/0175536 A1 | 8/2007 | Monetti et al. |
| 2007/0179507 A1 | 8/2007 | Shah |
| 2007/0179520 A1 | 8/2007 | West |
| 2007/0185442 A1 | 8/2007 | Euteneuer et al. |
| 2007/0185443 A1 | 8/2007 | Euteneuer et al. |
| 2007/0185444 A1 | 8/2007 | Euteneuer et al. |
| 2007/0185457 A1 | 8/2007 | Euteneuer et al. |
| 2007/0186933 A1 | 8/2007 | Domingo et al. |
| 2007/0191924 A1 | 8/2007 | Rudakov |
| 2007/0198059 A1 | 8/2007 | Patel et al. |
| 2007/0198075 A1 | 8/2007 | Levy |
| 2007/0219619 A1 | 9/2007 | Dieck et al. |
| 2007/0221230 A1 | 9/2007 | Thompson et al. |
| 2007/0265656 A1 | 11/2007 | Amplatz et al. |
| 2007/0270902 A1 | 11/2007 | Slazas et al. |
| 2007/0276426 A1 | 11/2007 | Euteneuer |
| 2007/0276427 A1 | 11/2007 | Euteneuer |
| 2007/0282373 A1 | 12/2007 | Ashby et al. |
| 2007/0288083 A1 | 12/2007 | Hines |
| 2007/0299461 A1 | 12/2007 | Elliott |
| 2008/0033366 A1 | 2/2008 | Matson et al. |
| 2008/0065145 A1 | 3/2008 | Carpenter |
| 2008/0081763 A1 | 4/2008 | Swetlin et al. |
| 2008/0082176 A1 | 4/2008 | Slazas |
| 2008/0086196 A1 | 4/2008 | Truckai et al. |
| 2008/0109057 A1 | 5/2008 | Calabria et al. |
| 2008/0114391 A1 | 5/2008 | Dieck et al. |
| 2008/0114436 A1 | 5/2008 | Dieck et al. |
| 2008/0119886 A1 | 5/2008 | Greenhalgh et al. |
| 2008/0125852 A1 | 5/2008 | Garrison et al. |
| 2008/0132820 A1 | 6/2008 | Buckman et al. |
| 2008/0140177 A1 | 6/2008 | Hines |
| 2008/0195137 A1 | 8/2008 | Alleyne et al. |
| 2008/0200945 A1 | 8/2008 | Amplatz et al. |
| 2008/0200979 A1 | 8/2008 | Dieck et al. |
| 2008/0221554 A1 | 9/2008 | OConnor et al. |
| 2008/0221600 A1 | 9/2008 | Dieck et al. |
| 2008/0221703 A1 | 9/2008 | Que et al. |
| 2008/0281350 A1 | 11/2008 | Sepetka et al. |
| 2008/0283066 A1 | 11/2008 | Delgado et al. |
| 2009/0018637 A1 | 1/2009 | Paul et al. |
| 2009/0024224 A1 | 1/2009 | Chen et al. |
| 2009/0025820 A1 | 1/2009 | Adams |
| 2009/0036877 A1 | 2/2009 | Nardone et al. |
| 2009/0043375 A1 | 2/2009 | Rudakov et al. |
| 2009/0056722 A1 | 3/2009 | Swann |
| 2009/0062899 A1 | 3/2009 | Dang et al. |
| 2009/0076540 A1 | 3/2009 | Marks et al. |
| 2009/0099592 A1 | 4/2009 | Buiser et al. |
| 2009/0112249 A1 | 4/2009 | Miles et al. |
| 2009/0112251 A1 | 4/2009 | Qian et al. |
| 2009/0125119 A1 | 5/2009 | Obermiller et al. |
| 2009/0148492 A1 | 6/2009 | Dave et al. |
| 2009/0155367 A1 | 6/2009 | Neuwirth et al. |
| 2009/0187214 A1 | 7/2009 | Amplatz et al. |
| 2009/0264978 A1 | 10/2009 | Dieck et al. |
| 2009/0270974 A1 | 10/2009 | Berez et al. |
| 2009/0275974 A1 | 11/2009 | Marchand et al. |
| 2009/0287291 A1 | 11/2009 | Becking et al. |
| 2009/0287292 A1 | 11/2009 | Becking et al. |
| 2009/0287294 A1 | 11/2009 | Rosqueta et al. |
| 2009/0287297 A1 | 11/2009 | Cox |
| 2009/0297582 A1 | 12/2009 | Meyer et al. |
| 2009/0306702 A1 | 12/2009 | Miloslavski et al. |
| 2009/0306706 A1 | 12/2009 | Osypka |
| 2009/0318892 A1 | 12/2009 | Aboytes et al. |
| 2009/0318941 A1 | 12/2009 | Sepetka et al. |
| 2009/0319023 A1 | 12/2009 | Hildebrand et al. |
| 2010/0021545 A1 | 1/2010 | Chaput et al. |
| 2010/0023046 A1 | 1/2010 | Heidner et al. |
| 2010/0023048 A1 | 1/2010 | Mach |
| 2010/0030200 A1 | 2/2010 | Strauss et al. |
| 2010/0036410 A1 | 2/2010 | Krolik et al. |
| 2010/0106178 A1 | 4/2010 | Obermiller et al. |
| 2010/0121350 A1 | 5/2010 | Mirigian |
| 2010/0131002 A1 | 5/2010 | Connor et al. |
| 2010/0139465 A1 | 6/2010 | Christian et al. |
| 2010/0144895 A1 | 6/2010 | Porter |
| 2010/0160949 A1 | 6/2010 | Takuma |
| 2010/0174269 A1 | 7/2010 | Tompkins et al. |
| 2010/0184720 A1 | 7/2010 | Gavard et al. |
| 2010/0185271 A1 | 7/2010 | Zhang |
| 2010/0228184 A1 | 9/2010 | Mavani et al. |
| 2010/0249830 A1 | 9/2010 | Nelson |
| 2010/0256527 A1 | 10/2010 | Lippert et al. |
| 2010/0256528 A1 | 10/2010 | Lippert et al. |
| 2010/0256601 A1 | 10/2010 | Lippert et al. |
| 2010/0256602 A1 | 10/2010 | Lippert et al. |
| 2010/0256603 A1 | 10/2010 | Lippert et al. |
| 2010/0256604 A1 | 10/2010 | Lippert et al. |
| 2010/0256605 A1 | 10/2010 | Lippert et al. |
| 2010/0256606 A1 | 10/2010 | Lippert et al. |
| 2010/0262014 A1 | 10/2010 | Huang |
| 2010/0268201 A1 | 10/2010 | Tieu et al. |
| 2010/0268251 A1 | 10/2010 | Chen et al. |
| 2010/0274276 A1 | 10/2010 | Chow et al. |
| 2010/0298791 A1 | 11/2010 | Jones et al. |
| 2010/0312061 A1 | 12/2010 | Hess et al. |
| 2011/0022149 A1 | 1/2011 | Cox et al. |
| 2011/0028378 A1 | 2/2011 | Hansen et al. |
| 2011/0046658 A1 | 2/2011 | Connor et al. |
| 2011/0077620 A1 | 3/2011 | Debeer |
| 2011/0125110 A1 | 5/2011 | Cotton |
| 2011/0137332 A1 | 6/2011 | Sepetka et al. |
| 2011/0137405 A1 | 6/2011 | Wilson et al. |
| 2011/0144669 A1 | 6/2011 | Becking et al. |
| 2011/0152993 A1 | 6/2011 | Marchand et al. |
| 2011/0166588 A1 | 7/2011 | Connor et al. |
| 2011/0196415 A1 | 8/2011 | Ujiie et al. |
| 2011/0202085 A1 | 8/2011 | Loganathan et al. |
| 2011/0208227 A1 | 8/2011 | Becking |
| 2011/0224776 A1 | 9/2011 | Sepetka et al. |
| 2011/0238041 A1 | 9/2011 | Lim et al. |
| 2011/0245862 A1 | 10/2011 | Dieck et al. |
| 2011/0251699 A1 | 10/2011 | Ladet |

(56) References Cited

U.S. PATENT DOCUMENTS

| | | |
|---|---|---|
| 2011/0265943 A1 | 11/2011 | Rosqueta et al. |
| 2011/0282378 A1 | 11/2011 | Murphy et al. |
| 2011/0319926 A1 | 12/2011 | Becking et al. |
| 2012/0010644 A1 | 1/2012 | Sideris et al. |
| 2012/0022572 A1 | 1/2012 | Braun et al. |
| 2012/0041472 A1 | 2/2012 | Tan et al. |
| 2012/0101510 A1 | 4/2012 | Lenker et al. |
| 2012/0116350 A1 | 5/2012 | Strauss et al. |
| 2012/0123510 A1 | 5/2012 | Liungman |
| 2012/0143237 A1 | 6/2012 | Cam et al. |
| 2012/0143243 A1 | 6/2012 | Hill et al. |
| 2012/0143301 A1 | 6/2012 | Maslanka et al. |
| 2012/0165919 A1 | 6/2012 | Cox et al. |
| 2012/0197283 A1 | 8/2012 | Marchand et al. |
| 2012/0239074 A1 | 9/2012 | Aboytes et al. |
| 2012/0271344 A1 | 10/2012 | Ford et al. |
| 2012/0283768 A1 | 11/2012 | Cox et al. |
| 2012/0283769 A1 | 11/2012 | Cruise et al. |
| 2012/0310269 A1 | 12/2012 | Fearnot et al. |
| 2012/0316598 A1 | 12/2012 | Becking et al. |
| 2012/0316632 A1 | 12/2012 | Gao |
| 2012/0323271 A1 | 12/2012 | Obermiller et al. |
| 2012/0330341 A1 | 12/2012 | Becking et al. |
| 2012/0330347 A1 | 12/2012 | Becking et al. |
| 2012/0330348 A1 | 12/2012 | Strauss et al. |
| 2013/0066357 A1 | 3/2013 | Aboytes et al. |
| 2013/0066360 A1 | 3/2013 | Becking et al. |
| 2013/0073026 A1 | 3/2013 | Russo et al. |
| 2013/0085522 A1 | 4/2013 | Becking et al. |
| 2013/0116722 A1 | 5/2013 | Aboytes et al. |
| 2013/0138136 A1 | 5/2013 | Beckham et al. |
| 2013/0211495 A1 | 8/2013 | Halden et al. |
| 2013/0244972 A1 | 9/2013 | Ben-Shalom et al. |
| 2013/0274866 A1 | 10/2013 | Cox et al. |
| 2014/0012307 A1 | 1/2014 | Franano et al. |
| 2014/0017210 A1 | 1/2014 | Laurencin et al. |
| 2014/0039542 A1 | 2/2014 | Trommeter et al. |
| 2014/0058420 A1 | 2/2014 | Hannes et al. |
| 2014/0135810 A1 | 5/2014 | Divino et al. |
| 2014/0135811 A1 | 5/2014 | Divino et al. |
| 2014/0135812 A1 | 5/2014 | Divino et al. |
| 2014/0200607 A1 | 7/2014 | Sepetka et al. |
| 2014/0215792 A1 | 8/2014 | Leopold et al. |
| 2014/0257360 A1 | 9/2014 | Keillor |
| 2014/0257361 A1 | 9/2014 | Prom |
| 2014/0257374 A1 | 9/2014 | Heisel et al. |
| 2014/0316012 A1 | 10/2014 | Freyman et al. |
| 2014/0371734 A1 | 12/2014 | Truckai |
| 2014/0377187 A1 | 12/2014 | Lerouge et al. |
| 2015/0005808 A1 | 1/2015 | Chouinard et al. |
| 2015/0133989 A1 | 5/2015 | Lubock et al. |
| 2015/0216684 A1 | 8/2015 | Enzmann et al. |
| 2015/0250628 A1 | 9/2015 | Monstadt et al. |
| 2015/0272589 A1 | 10/2015 | Lorenzo |
| 2015/0272590 A1 | 10/2015 | Aboytes et al. |
| 2015/0313605 A1 | 11/2015 | Griffin |
| 2015/0313737 A1 | 11/2015 | Tippett et al. |
| 2015/0327843 A1 | 11/2015 | Garrison |
| 2015/0335333 A1 | 11/2015 | Jones et al. |
| 2015/0342613 A1 | 12/2015 | Aboytes et al. |
| 2015/0343181 A1 | 12/2015 | Bradway et al. |
| 2016/0022445 A1 | 1/2016 | Ruvalcaba et al. |
| 2016/0030050 A1 | 2/2016 | Franano et al. |
| 2016/0066921 A1 | 3/2016 | Seifert et al. |
| 2016/0106437 A1 | 4/2016 | Van Der Burg et al. |
| 2016/0128699 A1 | 5/2016 | Hadley et al. |
| 2016/0135984 A1 | 5/2016 | Rudakov et al. |
| 2016/0206320 A1 | 7/2016 | Connor |
| 2016/0206321 A1 | 7/2016 | Connor |
| 2016/0249935 A1* | 9/2016 | Hewitt ............... A61B 17/1215 606/200 |
| 2016/0256170 A1 | 9/2016 | Busold et al. |
| 2016/0296714 A1 | 10/2016 | Mide et al. |
| 2016/0331381 A1 | 11/2016 | Ma |
| 2017/0105739 A1 | 4/2017 | Dias et al. |

| | | |
|---|---|---|
| 2017/0150971 A1 | 6/2017 | Hines |
| 2017/0156734 A1 | 6/2017 | Griffin |
| 2017/0156903 A1 | 6/2017 | Shobayashi |
| 2017/0189035 A1 | 7/2017 | Porter |
| 2017/0224350 A1 | 8/2017 | Shimizu et al. |
| 2017/0224355 A1 | 8/2017 | Bowman et al. |
| 2017/0266023 A1 | 9/2017 | Thomas |
| 2017/0296466 A1 | 10/2017 | Girdhar et al. |
| 2017/0312364 A1 | 11/2017 | Bossy et al. |
| 2017/0340333 A1 | 11/2017 | Badruddin et al. |
| 2017/0354419 A1 | 12/2017 | Teoh et al. |
| 2017/0354421 A1 | 12/2017 | Maguire et al. |
| 2017/0367704 A1 | 12/2017 | Rhee et al. |
| 2017/0367707 A1 | 12/2017 | Divino |
| 2017/0367708 A1 | 12/2017 | Mayer et al. |
| 2017/0367713 A1 | 12/2017 | Greene et al. |
| 2018/0049859 A1 | 2/2018 | Stoppenhagen et al. |
| 2018/0070955 A1 | 3/2018 | Greene et al. |
| 2018/0110797 A1 | 4/2018 | Li et al. |
| 2018/0125686 A1 | 5/2018 | Lu |
| 2018/0132856 A1 | 5/2018 | Wierzbicki et al. |
| 2018/0140305 A1 | 5/2018 | Connor |
| 2018/0161185 A1 | 6/2018 | Kresslein et al. |
| 2018/0193025 A1 | 7/2018 | Walzman |
| 2018/0193026 A1 | 7/2018 | Yang et al. |
| 2018/0206849 A1 | 7/2018 | Hewitt et al. |
| 2018/0206852 A1 | 7/2018 | Moeller |
| 2018/0242979 A1 | 8/2018 | Lorenzo |
| 2018/0256171 A1 | 9/2018 | Chow et al. |
| 2018/0317932 A1 | 11/2018 | H'Doubler |
| 2019/0008522 A1 | 1/2019 | Lorenzo |
| 2019/0009057 A1 | 1/2019 | Li et al. |
| 2019/0053807 A1 | 2/2019 | Tassoni et al. |
| 2019/0053811 A1 | 2/2019 | Garza et al. |
| 2019/0192167 A1* | 6/2019 | Lorenzo ........... A61B 17/12031 |
| 2019/0223876 A1 | 7/2019 | Badruddin et al. |
| 2019/0223881 A1 | 7/2019 | Hewitt et al. |
| 2019/0282242 A1 | 9/2019 | Divino et al. |
| 2019/0343532 A1 | 11/2019 | Divino et al. |
| 2019/0351107 A1 | 11/2019 | Sawhney et al. |
| 2020/0060965 A1 | 2/2020 | Supper |
| 2020/0061099 A1 | 2/2020 | Li et al. |
| 2020/0113576 A1 | 4/2020 | Gorochow et al. |
| 2020/0138448 A1 | 5/2020 | Dasnurkar et al. |
| 2020/0268392 A1 | 8/2020 | Choi et al. |
| 2020/0315644 A1 | 10/2020 | Bowman |
| 2020/0360419 A1 | 11/2020 | Mccarthy et al. |
| 2021/0022743 A1 | 1/2021 | Delaney et al. |
| 2021/0128160 A1 | 5/2021 | Li et al. |
| 2021/0128161 A1 | 5/2021 | Nageswaran et al. |
| 2021/0128162 A1 | 5/2021 | Rhee et al. |
| 2021/0128165 A1 | 5/2021 | Pulugurtha et al. |
| 2021/0128167 A1 | 5/2021 | Patel et al. |
| 2021/0128168 A1 | 5/2021 | Nguyen et al. |
| 2021/0128169 A1 | 5/2021 | Li et al. |
| 2021/0129275 A1 | 5/2021 | Nguyen et al. |
| 2021/0137530 A1 | 5/2021 | Greene et al. |
| 2021/0153872 A1 | 5/2021 | Nguyen et al. |
| 2021/0161643 A1 | 6/2021 | Totten et al. |
| 2021/0196284 A1 | 7/2021 | Gorochow et al. |
| 2021/0212698 A1 | 7/2021 | Connor |
| 2022/0008082 A1 | 1/2022 | Connor |
| 2022/0296788 A1 | 9/2022 | Hussain et al. |
| 2022/0304696 A2 | 9/2022 | Rhee et al. |
| 2023/0023511 A1 | 1/2023 | Nguyen et al. |
| 2023/0294223 A1 | 9/2023 | Li et al. |
| 2023/0301660 A1 | 9/2023 | Sonmez et al. |
| 2023/0311254 A1 | 10/2023 | Nguyen et al. |
| 2023/0373040 A1 | 11/2023 | Nguyen et al. |
| 2024/0050099 A1 | 2/2024 | Pecor et al. |
| 2025/0169824 A1 | 5/2025 | Li et al. |
| 2025/0195077 A1 | 6/2025 | Nguyen et al. |
| 2025/0241649 A1 | 7/2025 | Nguyen et al. |

FOREIGN PATENT DOCUMENTS

| | | |
|---|---|---|
| CN | 101460102 A | 6/2009 |
| CN | 102083493 A | 6/2011 |
| CN | 102202585 A | 9/2011 |

(56)          References Cited

FOREIGN PATENT DOCUMENTS

| | | | |
|---|---|---|---|
| CN | 202313544 | U | 7/2012 |
| CN | 102740799 | A | 10/2012 |
| CN | 105105812 | A | 12/2015 |
| CN | 105209075 | A | 12/2015 |
| DE | 102011102933 | A1 | 12/2012 |
| EP | 0717969 | A2 | 6/1996 |
| EP | 1188414 | A1 | 3/2002 |
| EP | 1813213 | A2 | 8/2007 |
| EP | 2208483 | A1 | 7/2010 |
| EP | 1448607 | B1 | 1/2011 |
| EP | 2566454 | B1 | 3/2014 |
| EP | 2468348 | B1 | 10/2016 |
| EP | 2121026 | B1 | 6/2017 |
| JP | 2005261951 | A | 9/2005 |
| JP | 2008521492 | A | 6/2008 |
| WO | 9406502 | A2 | 3/1994 |
| WO | 9905977 | A1 | 2/1999 |
| WO | 03011151 | A1 | 2/2003 |
| WO | 2006034149 | A2 | 3/2006 |
| WO | 2007006139 | A1 | 1/2007 |
| WO | 2007079402 | A2 | 7/2007 |
| WO | 2007121405 | A2 | 10/2007 |
| WO | 2008074027 | A1 | 6/2008 |
| WO | 2009014528 | A1 | 1/2009 |
| WO | 2009134337 | A1 | 11/2009 |
| WO | 2010009019 | A1 | 1/2010 |
| WO | 2010027363 | A1 | 3/2010 |
| WO | 2010028300 | A1 | 3/2010 |
| WO | 2010077599 | A1 | 7/2010 |
| WO | 2011066962 | A1 | 6/2011 |
| WO | 2011095966 | A1 | 8/2011 |
| WO | 2012034135 | A1 | 3/2012 |
| WO | 2013112944 | A1 | 8/2013 |
| WO | 2013138615 | A2 | 9/2013 |
| WO | 2013138615 | A3 | 9/2014 |
| WO | 2014169708 | A1 | 10/2014 |
| WO | 2015160721 | A1 | 10/2015 |
| WO | 2015166013 | A1 | 11/2015 |
| WO | 2016098057 | A1 | 6/2016 |
| WO | 2017074411 | A1 | 5/2017 |
| WO | 2018050262 | A1 | 3/2018 |
| WO | 2018051187 | A1 | 3/2018 |
| WO | 2019038293 | A1 | 2/2019 |
| WO | 2020162764 | A1 | 8/2020 |
| WO | 2020236917 | A1 | 11/2020 |
| WO | 2020262817 | A1 | 12/2020 |
| WO | 2021046389 | A1 | 3/2021 |

OTHER PUBLICATIONS

International Search Report and Written Opinion mailed Aug. 9, 2022; International Application No. PCT/US2022/071166; 10 pages.

International Search Report and Written Opinion mailed Feb. 17, 2021, International Application No. PCT/US20/70741, 6 pages.

International Search Report and Written Opinion mailed Feb. 23, 2021, International Application No. PCT/US20/70743, 14 pages.

Medtronic ENT. (2021). Discover Novapak: Beyond Structural Stability [Brochure]. Medtronic.

International Search Report and Written Opinion mailed Apr. 13, 2021, International Application No. PCT/US20/70742,18 pages.

Barnett, et al., "Assessment of EmboGel—A Selectively Dissolvable Radiopaque Hydrogel for Embolic Applications", J Vasc Interv Radiol 2011; vol. 22, No. 2, Feb. 2011, pp. 203-211.

Berenstein, et al., "Treatment of Experimental Aneurysms With an Embolic-Containing Device and Liquid Embolic Agent: Feasibility and Angiographic and Histological Results", Neurosurgery, vol. 64, No. 2, Feb. 2009, pp. 367-373.

Brennecka, et al., "In vivo embolization of lateral wall aneurysms in canines using the liquid-to-solid gelling PPODA-QT polymer system: 6-month pilot study", Laboratory investigation, J Neurosurg, vol. 119,, Jul. 2013, pp. 228-238.

Coutu, et al., "A new radiopaque embolizing agent for the treatment of endoleaks after endovascular repair: Influence of contrast agent on chitosan thermogel properties", Journal of Biomedical Materials Research Part B: Applied Biomaterials, 101B(1), 153-161. https://doi.org/10.1002/jbm.b.32828.

Jalani, et al., "Tough, In-Situ Thermogelling, Injectable Hydrogels for Biomedical Applications", Macromolecular Bioscience, 2014, 8 Pages.

Murayama, et al., "Endovascular Treatment of Experimental Aneurysms by Use of a Combination of Liquid Embolic Agents and Protective Devices", Experimental Aneurysms, AJNR Am J Neuroradiol, vol. 21, Oct. 2000, pp. 1726-1735.

Ning, et al., "Experimental study of temperature-sensitive chitosan/β-glycerophosphate embolic material in embolizing the basicranial rete mirabile in swines", Experimental and Therapeutic Medicine, vol. 10, Feb. 19, 2015, pp. 316-322.

Shive, et al., "BST-Cargel® treatment maintains cartilage repair superiority over microfracture at 5 years in a multicenter randomized controlled trial.", Cartilage, 6(2), 62-72. https://doi.org/10.1177/1947603514562064.

Supper, et al., "Chitosan/glucose 1-phosphate as new stable in situ forming depot system for controlled drug delivery", European Journal of Pharmaceutics and Biopharmaceutics, 88(2), 361-373. https://doi.org/10.1016/j.ejpb.2014.05.015.

Supper, et al., "Rheological Study of Chitosan/Polyol-phosphate Systems: Influence of the Polyol Part on the Thermo-Induced Gelation Mechanism", Langmuir, 29(32), 10229-10237. https://doi.org/10.1021/la401993q.

Wang, et al., "In Vivo Assessment of Chitosan/β-Glycerophosphate as a New Liquid Embolic Agent", Interventional Neuroradiology, vol. 17, 2011, pp. 87-92.

Zhen, et al., "Embolization of aneurysm by chitosan-glycerophosphate-fibroblast tissue hydrogel, a tissue engineering material: experiment with rabbits", Natl Med J China, vol. 89, No. 11, Mar. 24, 2009, pp. 727-731.

* cited by examiner

SYSTEMS AND METHODS FOR TREATING ANEURYSMS

CROSS-REFERENCE TO RELATED APPLICATIONS

The present application is a continuation of U.S. patent application Ser. No. 16/949,561, filed Nov. 3, 2020, which claims the benefit of priority of U.S. Provisional Application No. 62/930,421, filed Nov. 4, 2019, U.S. Provisional Application No. 62/930,487, filed Nov. 4, 2019, U.S. Provisional Application No. 62/930,303, filed Nov. 4, 2019, U.S. Provisional Application No. 62/930,324, filed Nov. 4, 2019, U.S. Provisional Application No. 62/930,333, filed Nov. 4, 2019, and U.S. Provisional Application No. 62/930,357, filed Nov. 4, 2019, each of which is incorporated by reference herein in its entirety.

The following applications are also incorporated by reference herein in their entireties: U.S. patent application Ser. No. 16/949,567, filed Nov. 3, 2020, and titled DEVICES, SYSTEMS, AND METHODS FOR TREATMENT OF INTRACRANIAL ANEURYSMS; U.S. patent application Ser. No. 16/949,568, filed Nov. 3, 2020, and titled DEVICES, SYSTEMS, AND METHODS FOR TREATMENT OF INTRACRANIAL ANEURYSMS; U.S. patent application Ser. No. 16/949,563, filed Nov. 3, 2020, and titled SYSTEMS AND METHODS FOR TREATING ANEURYSMS; U.S. patent application Ser. No. 16/949,564, filed Nov. 3, 2020, and titled SYSTEMS AND METHODS FOR TREATING ANEURYSMS; U.S. patent application Ser. No. 16/949,565, filed Nov. 3, 2020, and titled ANEURYSM TREATMENT DEVICE; U.S. patent application Ser. No. 16/949,569, filed Nov. 3, 2020, and titled DEVICES, SYSTEMS, AND METHODS FOR TREATMENT OF INTRACRANIAL ANEURYSMS; U.S. patent application Ser. No. 16/949,566, filed Nov. 3, 2020, and titled SYSTEMS AND METHODS FOR TREATING ANEURYSMS; U.S. patent application Ser. No. 16/949,570, filed Nov. 3, 2020, and titled DEVICES, SYSTEMS, AND METHODS FOR TREATING ANEURYSMS; International Application No. PCT/US2020/070743, filed Nov. 3, 2020, titled DEVICES, SYSTEMS, AND METHODS FOR TREATMENT OF INTRACRANIAL ANEURYSMS; International Application No. PCT/US2020/070741, filed Nov. 3, 2020, titled DEVICES, SYSTEMS, AND METHODS FOR TREATMENT OF INTRACRANIAL ANEURYSMS; and International Application No. PCT/US2020/070742, filed Nov. 3, 2020, titled SYSTEMS AND METHODS FOR TREATING ANEURYSMS.

TECHNICAL FIELD

The present technology relates to systems, devices, and methods for treating intracranial aneurysms.

BACKGROUND

An intracranial aneurysm is a portion of an intracranial blood vessel that bulges outward from the blood vessel's main channel. This condition often occurs at a portion of a blood vessel that is abnormally weak because of a congenital anomaly, trauma, high blood pressure, or for another reason. Once an intracranial aneurysm forms, there is a significant risk that the aneurysm will eventually rupture and cause a medical emergency with a high risk of mortality due to hemorrhaging. When an unruptured intracranial aneurysm is detected or when a patient survives an initial rupture of an intracranial aneurysm, vascular surgery is often indicated. One conventional type of vascular surgery for treating an intracranial aneurysm includes using a microcatheter to dispose a platinum coil within an interior volume of the aneurysm. Over time, the presence of the coil should induce formation of a thrombus. Ideally, the aneurysm's neck closes at the site of the thrombus and is replaced with new endothelial tissue. Blood then bypasses the aneurysm, thereby reducing the risk of aneurysm rupture (or re-rupture) and associated hemorrhaging. Unfortunately, long-term recanalization (i.e., restoration of blood flow to the interior volume of the aneurysm) after this type of vascular surgery occurs in a number of cases, especially for intracranial aneurysms with relatively wide necks and/or relatively large interior volumes.

Another conventional type of vascular surgery for treating an intracranial aneurysm includes deploying a flow diverter within the associated intracranial blood vessel. The flow diverter is often a mesh tube that causes blood to preferentially flow along a main channel of the blood vessel while blood within the aneurysm stagnates. The stagnant blood within the aneurysm should eventually form a thrombus that leads to closure of the aneurysm's neck and to growth of new endothelial tissue, as with the platinum coil treatment. One significant drawback of flow diverters is that it may take weeks or months to form aneurysmal thrombus and significantly longer for the aneurysm neck to be covered with endothelial cells for full effect. This delay may be unacceptable when risk of aneurysm rupture (or re-rupture) is high. Moreover, flow diverters typically require antiplatelet therapy to prevent a thrombus from forming within the main channel of the blood vessel at the site of the flow diverter. Antiplatelet therapy may be contraindicated shortly after an initial aneurysm rupture has occurred because risk of re-rupture at this time is high and antiplatelet therapy tends to exacerbate intracranial hemorrhaging if re-rupture occurs. For these and other reasons, there is a need for innovation in the treatment of intracranial aneurysms. Given the severity of this condition, innovation in this field has immediate life-saving potential.

SUMMARY

The present technology is illustrated, for example, according to various aspects described below. Various examples of aspects of the present technology are described as numbered clauses (1, 2, 3, etc.) for convenience. These are provided as examples and do not limit the present technology. It is noted that any of the dependent clauses may be combined in any combination, and placed into a respective independent clause. The other clauses can be presented in a similar manner.

1. A treatment system comprising:
an electrolytically corrodible core wire having a proximal portion, a distal portion, and a detachment zone between the proximal portion and the distal portion;
an occlusive member having a proximal hub coupled to the core wire distal portion, the occlusive member configured to be positioned at or adjacent to a treatment site; and
a conduit extending along at least a portion of the core wire, the conduit having a lumen configured to pass an embolic element therethrough.

2. The treatment system of any one of the previous Clauses, wherein a distal portion of conduit is configured to be disposed at or adjacent the treatment site alongside the occlusive member.

3. The treatment system of any one of the previous Clauses, wherein the treatment site comprises an aneurysm sac.

4. The treatment system of any one of the previous Clauses, wherein the conduit comprises a flexible tubular member.

5. The treatment system of any one of the previous Clauses, further comprising a stylet configured to be removably disposed within the lumen of the conduit.

6. The treatment system of any one of the previous Clauses, wherein the stylet is more rigid than the conduit.

7. The treatment system of any one of the previous Clauses, wherein the stylet is metallic.

8. The treatment system of any one of the previous Clauses, wherein the conduit has a distal portion having a smaller cross-sectional dimension than a proximal portion of the conduit.

9. The treatment system of any one of the previous Clauses, wherein the stylet has a distal portion having a smaller cross-sectional dimension than a proximal portion of the stylet.

10. The treatment system of any one of the previous Clauses, wherein the conduit is coupled to the elongated member such that the two cannot slide relative to one another.

11. The treatment system of any one of the previous Clauses, wherein the conduit is coupled to the elongated member via one or more bands or clamps.

12. The treatment system of any one of the previous Clauses, wherein the one or more bands or clamps circumferentially surround both the conduit and the core wire.

13. The treatment system of any one of the previous Clauses, wherein the conduit is coupled to the elongated member via an adhesive.

14. The treatment system of any one of the previous Clauses, wherein the conduit is coupled to the elongated member via a surrounding sheath.

15. The treatment system of any one of the previous Clauses, wherein the surrounding sheath comprises a heat-shrink polymer.

16. The treatment system of any one of the previous Clauses, wherein the heat-shrink polymer comprises PTFE.

17. The treatment system of any one of the previous Clauses, wherein the conduit comprises a tubular member, a hypotube, and/or a catheter.

18. The treatment system of any one of the previous Clauses, wherein the conduit comprises a liner extending through a lumen of a tubular member, the liner extending distally beyond a distal end of the tubular member.

19. The treatment system of any one of the previous Clauses, wherein the liner comprises extruded PTFE.

20. The treatment system of any one of the previous Clauses, wherein the conduit has an inner diameter along at least a portion of its length of between 0.005 inches and 0.015 inches.

21. The treatment system of any one of the previous Clauses, wherein the core wire comprises a proximal insulating layer annularly contacting the proximal portion of the core wire and a distal insulating layer annularly contacting the distal portion of the core wire.

22. The treatment system of any one of the previous Clauses, wherein the detachment zone has a microstructure with lower crystallinity than proximal and distal portions of the core wire.

23. The treatment system of any one of the previous Clauses, wherein the detachment zone has a microstructure that is more amorphous than each of the core wire proximal portion and the core wire distal portion.

24. The treatment system of any one of the previous Clauses, wherein the core wire is made of an electrically conductive material.

25. The treatment system of any one of the previous Clauses, wherein the detachment zone has an axial length that is less than 0.010 inches.

26. The treatment system of any one of the previous Clauses, wherein the detachment zone has an axial length greater than or equal to 0.005 inches and less than 0.010 inches.

27. The treatment system of any one of the previous Clauses, wherein the core wire comprises an anchor end that is distal to a distalmost end of the hub, the anchor end having a maximum cross-sectional dimension that is greater than an inner cross-sectional dimension of a lumen of the hub.

28. The treatment system of any one of the previous Clauses, wherein the detachment zone is axially between the core wire proximal portion and the core wire distal portion 29. The treatment system of any one of the previous Clauses, wherein the occlusive member is an occlusive member or intrasaccular device configured to be implanted within an aneurysm.

30. The treatment system of any one of the previous Clauses, wherein the occlusive member comprises an expandable mesh having a constrained state for delivery to an aneurysm and an expanded state in which at least a portion of the mesh is configured to be disposed across a neck of the aneurysm.

31. The treatment system of any one of the previous Clauses, wherein the expandable mesh comprises a plurality of braided filaments that assume a pre-set, three-dimensional shape in the expanded state.

32. The treatment system of any one of the previous Clauses, wherein the expandable mesh comprises a braid formed of 24, 32, 36, 48, 64, or 72 filaments.

33. The treatment system of any one of the previous Clauses, wherein the expandable mesh comprises a braid formed of a plurality of wires, some or all of which have a diameter of at least 0.001 inches.

34. The treatment system of any one of the previous Clauses, wherein the expandable mesh comprises a braid formed of a plurality of wires, some or all of which have the same diameter.

35. The treatment system of any one of the previous Clauses, wherein the expandable mesh comprises a braid formed of a plurality of wires, at least some of which have different diameters.

36. The treatment system of any one of the previous Clauses, wherein, in the expanded state, the expandable mesh forms one of a sphere, a prolate spheroid, or an oblate spheroid.

37. The treatment system of any one of the previous Clauses, wherein the expandable mesh comprises an inner layer and an outer layer.

38. The treatment system of any one of the previous Clauses, wherein the expandable mesh has a maximum cross-sectional dimension of 3.0 mm, 3.5 mm, 4.0 mm, 4.5 mm, 5.0 mm, 5.5 mm, 6.0 mm, 6.5 mm, 7.0 mm, 7.5 mm, or 8.0 mm.

39. The treatment system of any one of the previous Clauses, wherein the expandable mesh is a laser-cut tube.

40. The treatment system of any one of the previous Clauses, wherein the expandable mesh comprises a plurality of interwoven filaments.

41. The treatment system of any one of the previous Clauses, wherein the occlusive member is curved along at least a majority of its entire length.

42. The treatment system of any one of the previous Clauses, wherein the occlusive member is collapsible when contacted by an embolic element.

43. The treatment system of any one of the previous Clauses, wherein the occlusive member is collapsible when contacted by a synthetic gel or fluid.

44. The treatment system of any one of the previous Clauses, wherein the occlusive member is configured to rotate about the conduit.

45. The treatment system of any one of the previous Clauses, wherein the occlusive member is rotatably and slidably coupled to the conduit.

46. The treatment system of any one of the previous Clauses, wherein the occlusive member has an aperture at a distal portion thereof, and wherein the conduit extends through the aperture.

47. The treatment system of any one of the previous Clauses, wherein the occlusive member is configured to move axially along the elongated member.

48. The treatment system of any one of the previous Clauses, wherein the embolic element is a liquid embolic.

49. The treatment system of any one of the previous Clauses, wherein the embolic element comprises a biopolymer and/or a chemical crosslinking agent.

50. The treatment system of any one of the previous Clauses, wherein the biopolymer includes chitosan, a derivative of chitosan, an analog of chitosan, or a combination thereof.

51. The treatment system of any one of the previous Clauses, wherein the chemical crosslinking agent includes genipin, a derivative of genipin, an analog of genipin, or a combination thereof.

52. A system comprising:
the treatment system of any one of the previous Clauses; and
an elongated shaft having a lumen extending therethrough, wherein the treatment system is configured to be slidably disposed within the lumen of the elongated shaft.

53. A system comprising:
the treatment system of any one of the previous Clauses;
a first elongated shaft having a first lumen extending therethrough, wherein the treatment system is configured to be slidably disposed within the first lumen; and
a second elongated shaft having a second lumen extending therethrough, wherein the first elongated shaft is configured to be slidably disposed within the second lumen.

54. The system of 32, wherein the first elongated shaft is a microcatheter and the second elongated shaft is a delivery or guide catheter.

55. The system of any one of the previous Clauses, wherein the microcatheter has a nominal inner diameter of about 0.017 inches or less, about 0.021 inches or less, or about 0.027 inches or less.

56. A method for treating an aneurysm, comprising:
providing the treatment system of any one of the previous Clauses.

57. The method of any one of the previous Clauses, further comprising:
positioning a distal end of the conduit in an aneurysm cavity; and
releasing the occlusive member from the elongated member while the distal end of the elongated member is positioned within the aneurysm cavity such that the occlusive member self-expands to assume an expanded state.

58. The method of any one of the previous Clauses, wherein releasing the occlusive member comprises electrolytically corroding the detachment zone of the core wire.

59. The method of any one of the previous Clauses, wherein releasing the occlusive member comprises delivering electrical current to the core wire.

60. The method of any one of the previous Clauses, wherein positioning the distal end of the conduit comprises advancing the distal end of the conduit toward a dome or distalmost end of the aneurysm, such that the distal end of the conduit extends beyond a distal terminus of a microcatheter surrounding the conduit.

61. The method of any one of the previous Clauses, further comprising positioning a distal end of the conduit in the aneurysm cavity along with the occlusive member.

62. The method of any one of the previous Clauses, wherein positioning the distal end of the conduit comprises distally advancing the conduit with a stylet disposed therein.

63. The method of any one of the previous Clauses, further comprising proximally retracting the stylet with respect to the conduit.

64. The method of any one of the previous Clauses, further comprising removing the stylet from within the lumen of the conduit.

65. The method of any one of the previous Clauses, wherein releasing the occlusive member comprises allowing the occlusive member to self-expand to assume a first expanded state in which the occlusive member forms a first shape, wherein, in the first expanded state, the occlusive member encloses an interior region having a first interior volume, the method further comprising
delivering an embolic element between the occlusive member and the aneurysm wall to transform the occlusive member into a second expanded state in which the occlusive member defines a second interior volume less than the first interior volume, wherein the occlusive member forms a second shape in the second expanded state that is different than the first shape in the first expanded state.

66. The method of any one of the previous Clauses, wherein transforming the occlusive member into the second expanded shape includes injecting the embolic material to urge a portion of a sidewall of the expandable mesh in a direction away from a wall of the aneurysm and towards the interior region of the occlusive member.

67. The method of any one of the previous Clauses, wherein transforming the occlusive member into the second expanded shape includes injecting the embolic material to invert a portion of a sidewall of the occlusive member such that the portion is convex towards the aneurysm wall in the first expanded state and concave towards the aneurysm wall in the second expanded state.

68. The method of any one of the previous Clauses, wherein the embolic element comprises a liquid embolic.

69. The method of any one of the previous Clauses, wherein the embolic element comprises one or more embolization coils.

70. The method of any one of the previous Clauses, wherein delivering the embolic element occurs after the occlusive member is in the first expanded state.

71. The method of any one of the previous Clauses, wherein the occlusive member is a mesh.

72. The method of any one of the previous Clauses, wherein the occlusive member is a braid.

73. The method of any one of the previous Clauses, wherein the occlusive member is a dual-layered braid.

74. The method of any one of the previous Clauses, wherein the occlusive member has a globular or generally spherical shape in the first expanded state.

75. The method of any one of the previous Clauses, wherein the occlusive member is cup or bowl-shaped in the second expanded state.

76. The method of any one of the previous Clauses, wherein the second shape is a predetermined three-dimensional shape.

77. The method of any one of the previous Clauses, wherein the occlusive member forms a multi-layer braid at the neck of the aneurysm in the second expanded state.

78. The method of any one of the previous Clauses, wherein the occlusive member comprises a plurality of braided filaments that assume a pre-set, three-dimensional shape in the expanded state.

79. The method of any one of the previous Clauses, wherein the occlusive member comprises a braid formed of 24, 32, 36, 48, 64, or 72 filaments.

80. The method of any one of the previous Clauses, wherein the occlusive member comprises a braid formed of a plurality of wires, some or all of which have a diameter of about 0.001 inches (0.00254 cm).

81. The method of any one of the previous Clauses, wherein the occlusive member comprises a braid formed of a plurality of wires, some or all of which have the same diameter.

82. The method of any one of the previous Clauses, wherein the occlusive member comprises a braid formed of a plurality of wires, at least some of which have different diameters.

83. The method of any one of the previous Clauses, wherein the occlusive member forms a closed, globular shape in the expanded state, the mesh having an aperture at a distal portion.

84. The method of any one of the previous Clauses, wherein, in the expanded state, the occlusive member forms one of a sphere, a prolate spheroid, or an oblate spheroid.

85. The method of any one of the previous Clauses, wherein the occlusive member comprises an inner layer and an outer layer.

86. The method of any one of the previous Clauses, wherein the occlusive member comprises an inner layer and an outer layer that meet at a fold at a distal portion of the occlusive member.

87. The method of any one of the previous Clauses, wherein the expandable mesh includes an aperture at a distal portion, the aperture being defined by the fold.

88. The method of any one of the previous Clauses, wherein the occlusive member comprises an inner layer and an outer layer that meet at a fold at a proximal portion of the occlusive member.

89. The method of any one of the previous Clauses, wherein the expandable mesh includes an aperture at a distal portion, the aperture being defined by the fold.

90. The method of any one of the previous Clauses, wherein the occlusive member has a maximum cross-sectional dimension of 3.0 mm, 3.5 mm, 4.0 mm, 4.5 mm, 5.0 mm, 5.5 mm, 6.0 mm, 6.5 mm, 7.0 mm, 7.5 mm, or 8.0 mm.

91. The method of any one of the previous Clauses, wherein the occlusive member is formed of a plurality of filaments having first and second ends fixed at the hub or a coupler.

92. The method of any one of the previous Clauses, wherein the occlusive member is formed of a plurality of filaments formed of an inner core material surrounded by an outer material.

93. The method of any one of the previous Clauses, wherein the inner core material is a radiopaque material and the outer material is a superelastic material.

94. The method of any one of the previous Clauses, wherein the occlusive member is a laser-cut tube.

95. The method of any one of the previous Clauses, wherein the occlusive member comprises a plurality of filaments.

96. The method of any one of the previous Clauses, wherein the filaments are interwoven.

97. The method of any one of the previous Clauses, wherein the filaments are braided.

98. The method of any one of the previous Clauses, wherein each of the filaments has a first end and a second end opposite the first end, and wherein both the first and second ends of the filaments are fixed relative to one another at a coupler.

99. The method of any one of the previous Clauses, wherein the coupler is disposed at a distal end of the occlusive member.

100. The method of any one of the previous Clauses, wherein the coupler is disposed at a proximal end of the occlusive member.

101. The method of any one of the previous Clauses, wherein each of the filaments terminate at only one end of the occlusive member.

102. The method of any one of the previous Clauses, wherein the filaments form an opening at an end of the occlusive member opposite the only one end.

103. The method of any one of the previous Clauses, wherein an inverted portion of each of the filaments define the opening.

104. The method of any one of the previous Clauses, wherein the inverted portions of the filaments are configured to move relative to one another.

105. The method of any one of the previous Clauses, wherein the embolic element comprises a biopolymer and a chemical crosslinking agent.

106. The method of any one of the previous Clauses, wherein the biopolymer includes chitosan, a derivative of chitosan, an analog of chitosan, or a combination thereof.

107. The method of any one of the previous Clauses, wherein the chemical crosslinking agent includes genipin, a derivative of genipin, an analog of genipin, or a combination thereof.

108. The method of any one of the previous Clauses, wherein the embolic element further comprises a physical crosslinking agent.

109. The method of any one of the previous Clauses, the physical crosslinking agent includes β glycerophosphate, a derivative of β glycerophosphate, an analog of β glycerophosphate, or a combination thereof.

110. The method of any one of the previous Clauses, wherein the biopolymer includes chitosan, a derivative of chitosan, an analog of chitosan, or a combination thereof;

the chemical crosslinking agent includes genipin, a derivative of genipin, an analog of genipin, or a combination thereof; and the physical crosslinking agent includes β glycerophosphate, a derivative of β glycerophosphate, an analog of β glycerophosphate, or a combination thereof.

111. The method of any one of the previous Clauses, wherein the embolic element comprises a contrast agent.

112. The method of any one of the previous Clauses, wherein the contrast agent is selected to provide diminishing radiopacity.

113. The method of any one of the previous Clauses, wherein the contrast agent includes iohexol, a derivative of iohexol, an analog of iohexol, or a combination thereof.

Additional features and advantages of the present technology are described below, and in part will be apparent from the description, or may be learned by practice of the present technology. The advantages of the present technology will be realized and attained by the structure particularly pointed out in the written description and claims hereof as well as the appended drawings.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

DETAILED DESCRIPTION

Figure 1A:
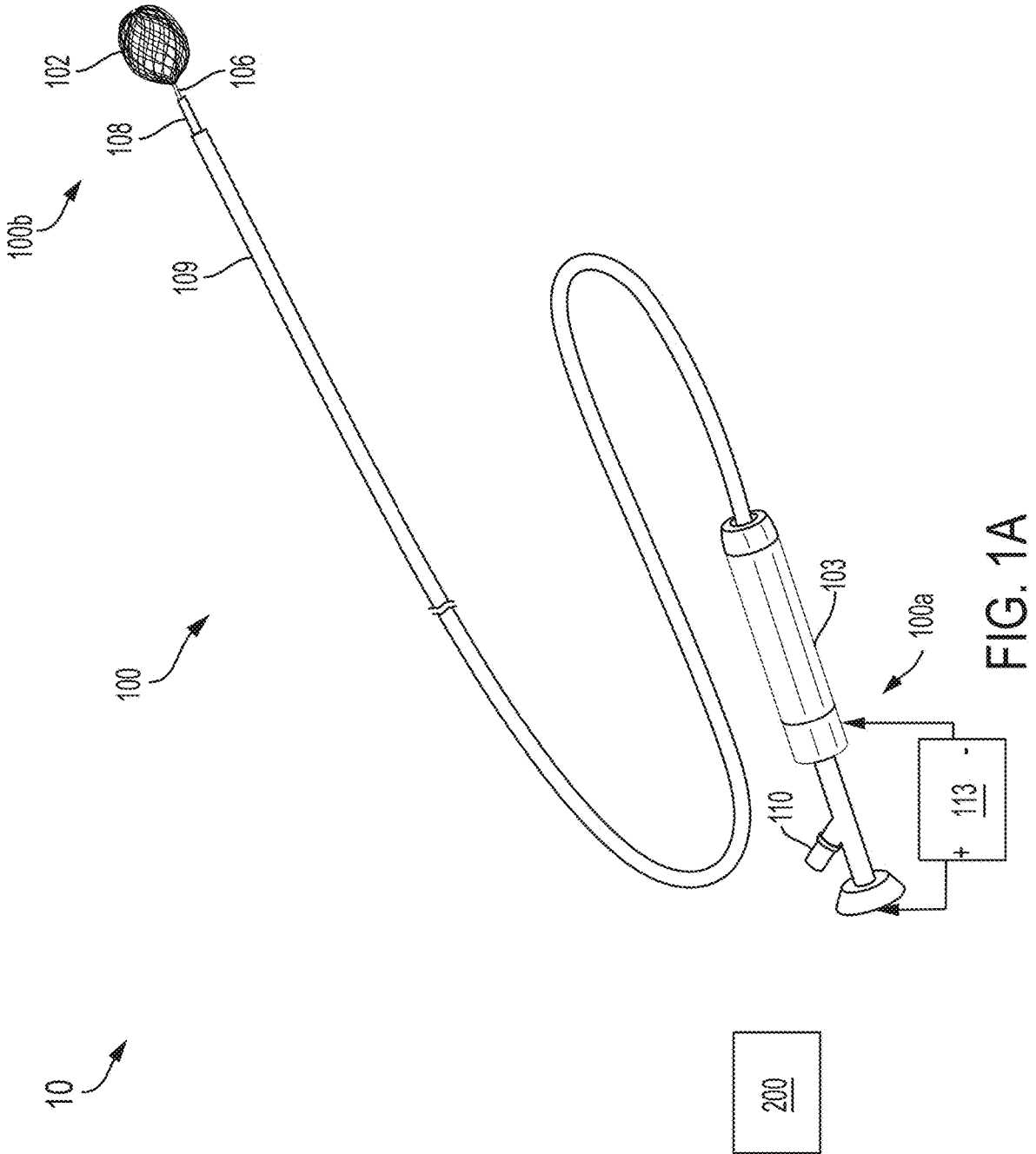
FIG. 1A shows a perspective view of a system for treating an aneurysm in accordance with the present technology.

Methods for treating intracranial aneurysms in accordance with at least some embodiments of the present technology include positioning an expandable occlusive member within the aneurysm and introducing an embolic element between the occlusive member and an aneurysm wall. Introduction of the embolic element both fills space within the aneurysm cavity and deforms the occlusive member from a first expanded state to a second expanded state to fortify the occlusive member at the neck of the aneurysm. Deformation of the occlusive member from a first expanded state to a second expanded state provides the additional advantage of giving visual confirmation to the physician that the delivered amount of embolic element sufficiently fills the aneurysm cavity. In addition to providing a structural support and anchor for the embolic element, the occlusive member provides a scaffold for tissue remodeling and diverts blood flow from the aneurysm. Moreover, the embolic element exerts a substantially uniform pressure on the occlusive member towards the neck of the aneurysm, thereby pressing the portions of the occlusive member positioned adjacent the neck against the inner surface of the aneurysm wall such that the occlusive member forms a complete and stable seal at the neck.

Once the occlusive member has deployed within the aneurysm and the embolic element has been delivered, the occlusive member may be detached from the delivery assembly. Suitable detachment mechanisms must be as small as possible so as to be guided through the fine bore of the catheter to the treatment site, while on the other hand they must securely and reliably produce detachment of the intrasaccular implant. Absent a reliable detachment of the intrasaccular implant, withdrawal of the core wire and catheter may cause unintended removal of the occlusive member from the cavity to be occluded and thus injure and/or rupture of the wall of the cavity or vessel. In some embodiments, an electrolytic detachment mechanism as described herein can be used to facilitate reliable, controlled detachment of the occlusive member.

The occlusive member can be implanted in body cavities or blood vessels. In addition to the occlusive member, the treatment system can comprise a voltage source, a cathode, a delivery conduit, and a catheter. The occlusive member and the delivery conduit can be coupled together such that both can be slid in the catheter in the longitudinal direction. A core wire may engage the occlusive member and be adapted to serve as an anode, such that a portion of the core wire is designed to be electrolytically corroded at one or more points so that while in contact with a body fluid, one or more portions of the occlusive member may be released from the core wire. The delivery conduit can be configured to run adjacent to the core wire along its length. The delivery conduit can be configured to pass one or more embolic elements therethrough for intrasaccular delivery. In some embodiments, a stylet can be removably disposed within the conduit to provide for enhanced rigidity and pushability of the conduit while it is being advanced to the treatment site. Once the stylet is removed, the embolic element may be passed through the conduit and delivered to the treatment site. Once the occlusive member and any embolic elements are deployed, current can be applied to the core wire to electrolytically corrode the core wire at a detachment zone. After the core wire has been severed at the detachment zone, the core wire and conduit can be retracted, and the occlusive member may remain in position at the treatment site.

Specific details of systems, devices, and methods for treating intracranial aneurysms in accordance with embodiments of the present technology are described herein with reference to FIGS. 1A-6. Although these systems, devices, and methods may be described herein primarily or entirely in the context of treating saccular intracranial aneurysms, other contexts are within the scope of the present technology. For example, suitable features of described systems, devices, and methods for treating saccular intracranial aneurysms can be implemented in the context of treating non-saccular intracranial aneurysms, abdominal aortic aneurysms, thoracic aortic aneurysms, renal artery aneurysms, arteriovenous malformations, tumors (e.g. via occlusion of vessel(s) feeding a tumor), perivascular leaks, varicose veins (e.g. via occlusion of one or more truncal veins such as the great saphenous vein), hemorrhoids, and sealing endoleaks adjacent to artificial heart valves, covered stents, and abdominal aortic aneurysm devices among other examples. Furthermore, it should be understood, in general, that other systems, devices, and methods in addition to those disclosed herein are within the scope of the present disclosure. For example, systems, devices, and methods in accordance with embodiments of the present technology can have different and/or additional configurations, components, procedures, etc. than those disclosed herein. Moreover, systems, devices, and methods in accordance with embodiments of the present disclosure can be without one or more of the configurations, components, procedures, etc. disclosed herein without deviating from the present technology.

I. OVERVIEW OF SYSTEMS OF THE PRESENT TECHNOLOGY

FIG. 1A illustrates a view of a system 10 for treating intracranial aneurysms according to one or more embodiments of the present technology. As shown in FIG. 1A, the system 10 comprises a treatment system 100 and an embolic kit 200 for use with one or more components of the treatment system 100. The treatment system 100 may comprise an occlusive member 102 (shown in an expanded state) detachably coupled to a delivery system, and the delivery system may be configured to intravascularly position the occlusive member 102 within an aneurysm. The embolic kit 200 may comprise one or more substances or devices that alone or in combination form an embolic element that is configured to co-occupy the internal volume of the aneurysm with the occlusive member 102. In some embodiments, the treatment system 100 may be configured to deliver the embolic element (and/or one or more precursors thereof) to the aneurysm. Additionally or alternatively, the system 10 may include a separate delivery system (not shown) for delivering the embolic element (and/or one or more precursors thereof) to the aneurysm cavity.

As shown in FIG. 1A, the treatment system 100 has a proximal portion 100a configured to be extracorporeally positioned during treatment and a distal portion 100b configured to be intravascularly positioned within a blood vessel (such as an intracranial blood vessel) at a treatment site at or proximate an aneurysm. The treatment system 100 may include a handle 103 at the proximal portion 100a, the occlusive member 102 at the distal portion 100b, and a plurality of elongated shafts or members extending between the proximal and distal portions 100a and 100b. In some embodiments, such as that shown in FIG. 1A, the treatment system 100 may include a first elongated shaft 109 (such as a guide catheter or balloon guide catheter), a second elongated shaft 108 (such as a microcatheter) configured to be slidably disposed within a lumen of the first elongated shaft 109, and an elongated member 106 configured to be slidably disposed within a lumen of the second elongated shaft 108. In some embodiments, the treatment system 100 does not include the first elongated shaft 109 and only includes the second elongated shaft 108.

Figure 1B:
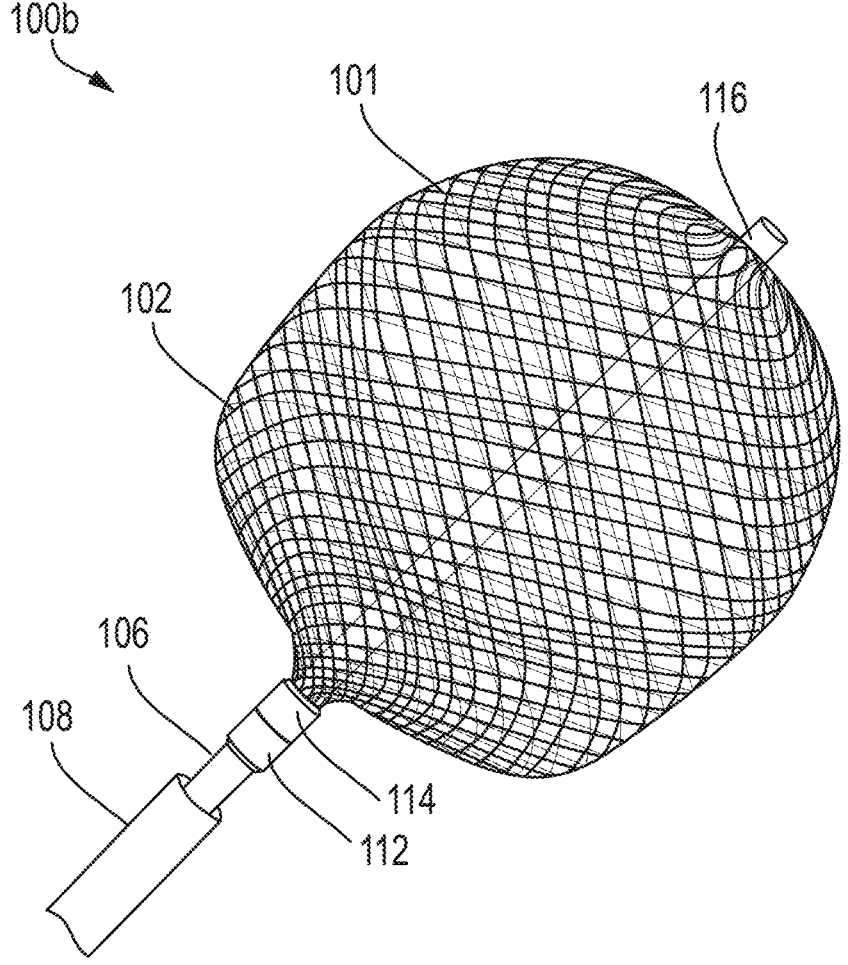
FIG. 1B shows an enlarged view of a distal portion of the treatment system of FIG. 1A in accordance with the present technology.

FIG. 1B is an enlarged view of the distal portion 100b of the treatment system 100. Referring to FIGS. 1A and 1B together, the occlusive member 102 may be detachably coupled to a distal end of the elongated member 106. For example, the elongated member 106 may include a first coupler 112 at its distal end, and the occlusive member 102 may include a second coupler 114 configured to detachably couple with the first coupler 112. In some embodiments, the couplers 112, 114 can take the form of an electrolytic detachment mechanism, for example as described in more detail below with respect to FIGS. 4A-6. The treatment system 100 may further comprise a conduit 116 extending from the handle 103 (for example, via port 110) distally to the distal portion 100b of the treatment system 100. The conduit 116 is configured to deliver the embolic element (and/or one or more precursors thereof) through one or more components of the delivery system (e.g., the first or second elongated shafts 109, 108, the elongated member 106, etc.) to a position at the exterior of the occlusive member 102. As such, the embolic element may be positioned between the occlusive member 102 and an inner wall of the aneurysm cavity, as described in greater detail below.

According to some embodiments, the second elongated shaft 108 is generally constructed to track over a conventional guidewire in the cervical anatomy and into the cerebral vessels associated with the brain and may also be chosen according to several standard designs that are generally available. Accordingly, the second elongated shaft 108 can have a length that is at least 125 cm long, and more particularly may be between about 125 cm and about 175 cm long. In some embodiments, the second elongated shaft 108 may have an inner diameter of about 0.015 inches (0.0381 cm), 0.017 inches (0.043 cm), about 0.021 inches (0.053 cm), or about 0.027 inches (0.069 cm). Other designs and dimensions are contemplated.

The elongated member 106 can be movable within the first and/or second elongated shafts 109, 108 to position the occlusive member 102 at a desired location. The elongated member 106 can be sufficiently flexible to allow manipulation, e.g., advancement and/or retraction, of the occlusive member 102 through tortuous passages. Tortuous passages can include, for example, catheter lumens, microcatheter lumens, blood vessels, urinary tracts, biliary tracts, and airways. The elongated member 106 can be formed of any material and in any dimensions suitable for the task(s) for which the system is to be employed. In some embodiments, the elongated member 106 can comprise a solid metal wire. In some embodiments, the elongated member 106 may comprise any other suitable form of shaft such as an elongated tubular shaft.

In some embodiments, the elongated member 106 can comprise stainless steel, nitinol, or other metal or alloy. In some embodiments, the elongated member 106 can be surrounded over some or all of its length by a coating, such as, for example, polytetrafluoroethylene. The elongated member 106 may have a diameter that is generally constant along its length, or the elongated member 106 may have a diameter that tapers radially inwardly, along at least a portion of its length, as it extends in a distal direction.

A power supply 113 may be coupled to a proximal portion of the elongated shaft 108, which can take the form of a conductive wire. The power supply 113 may also be coupled to a proximal portion of a handle or to the patient. A current can flow from the power supply 113, to a detachment zone at or near the occlusive member 102, and to a return path via the first elongated shaft 109, the second elongated shaft 108, and/or another structure extending near the detachment zone. Alternatively, the current from the detachment zone may flow to the patient, and subsequently to ground or to the power supply 113. Power supply 113, for example, may be a direct current power supply, an alternating current power supply, or a power supply switchable between a direct current and an alternating current. A positive terminal of a direct current power supply, as shown in FIG. 1, may be coupled to the proximal portion of the elongated shaft 108, 111 and a negative terminal of a direct current power supply may be coupled to the proximal portion of the handle. Power supply 113 may provide a current through the treatment system 100 to initiate an electrolytic process during use of the assembly in a fluid medium such as a bloodstream, which may be used as an electrolyte. A power supply, such as an alternating or direct current power supply, may additionally be used to initiate an electrothrombosis process.

According to several embodiments, the conduit 116 may be a catheter or elongated shaft that is delivered separately from the second elongated shaft 108.

A. Selected Examples of Occlusive Members

Figure 1C:
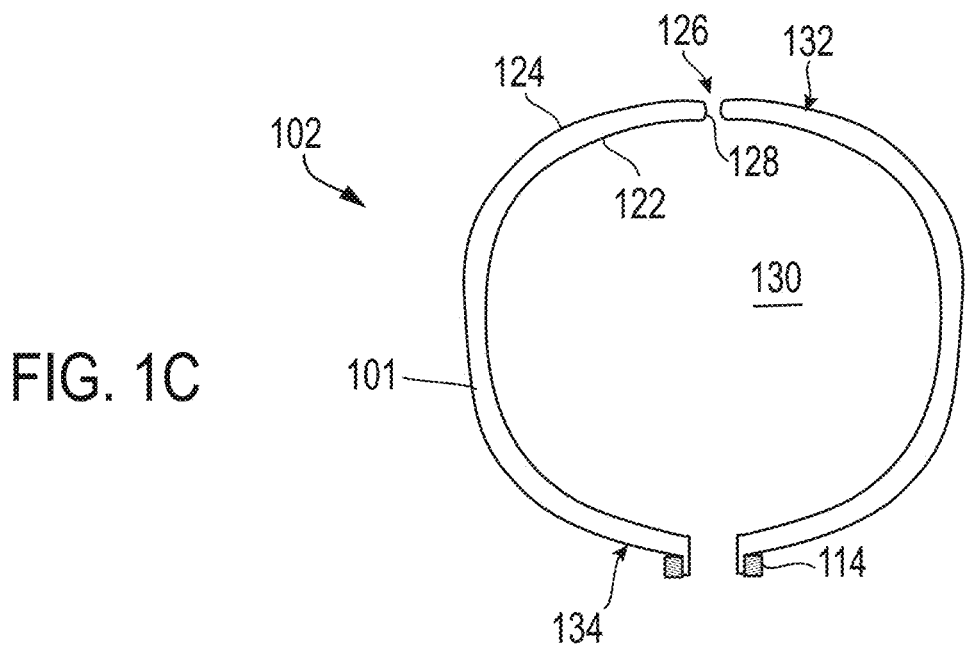
FIGS. 1C and 1D are sectioned views of occlusive members in an expanded state in accordance with the present technology.

FIG. 1C is a sectioned view of the occlusive member 102, shown in an expanded state and detached from the treatment system 100. Referring to FIGS. 1B and 1C, the occlusive member 102 may comprise an expandable element having a low-profile or constrained state while positioned within a catheter (such as the second elongated shaft 108) for delivery to the aneurysm and an expanded state in which the expandable element is configured to be positioned within an aneurysm (such as a cerebral aneurysm).

According to some embodiments, the occlusive member 102 may comprise a mesh 101 formed of a plurality of braided filaments that have been heat-set to assume a predetermined shape enclosing an interior volume 130 when the mesh 101 is in an expanded, unconstrained state. Example shapes include a globular shape, such as a sphere, a prolate spheroid, an oblate spheroid, and others. As depicted in FIG. 1C, the mesh 101 may have inner and outer layers 122, 124 that have proximal ends fixed relative to one another at the second coupler 114 and meet distally at a distal fold 128 surrounding an aperture 126. While the inner and outer layers 122, 124 are depicted spaced apart from one another along their lengths, the inner and outer layers 122, 124 may be in contact with one another along all or a portion of their lengths. For example, the inner layer 122 may press radially outwardly against the outer layer 124. In some embodiments, the occlusive member 102 may be formed of a single layer or mesh or braid.

In some embodiments, the inner and outer layers 122, 124 have their distal ends fixed relative to one another at a distal coupler and meet proximally at a proximal fold surrounding an aperture. In any case, in some embodiments the conduit 116 may be configured to be slidably positioned through some or all of the second coupler 114, the interior volume 130 of the expanded mesh 101, and the opening 126.

The inner and outer layers 122 and 124 may conform to one another at the distal portion (for example as shown in FIG. 1C) to form a curved distal surface. For example, at least at the distal portion of the occlusive member 102, the inner and outer layers 122 and 124 may extend distally and radially inwardly, towards the aperture 126. In some embodiments, the outer and/or inner layers 122 and 124 extend distally and radially outwardly from the second coupler 114, then extend distally and radially inwardly up to a distal terminus of the occlusive member 102 (e.g., the fold 128). The occlusive member 102 and/or layers thereof may be curved along its entire length, or may have one or more generally straight portions. In some embodiments, the curved surface transitions to a flat or substantially flat, distal-most surface that surrounds the aperture 126. In some embodiments, the curved surface transitions to a distal-most surface that surrounds the aperture 126 and has a radius of curvature that is greater than the average radius of curvature of the rest of the occlusive member 102. Having a flat or substantially flat distal surface, or a distal surface with a radius of curvature that is greater than the average radius of curvature of the rest of the occlusive member 102, may be beneficial for delivering the embolic element 230 in that it creates a small gap between the distal surface of the occlusive member 102 and the dome of the aneurysm A (see, for example, FIG. 3B). In some embodiments, the surface of the occlusive member 102 surrounding the aperture 126 is curved and/or has generally the same radius of curvature as the remainder of the occlusive member 102.

Figure 1D:
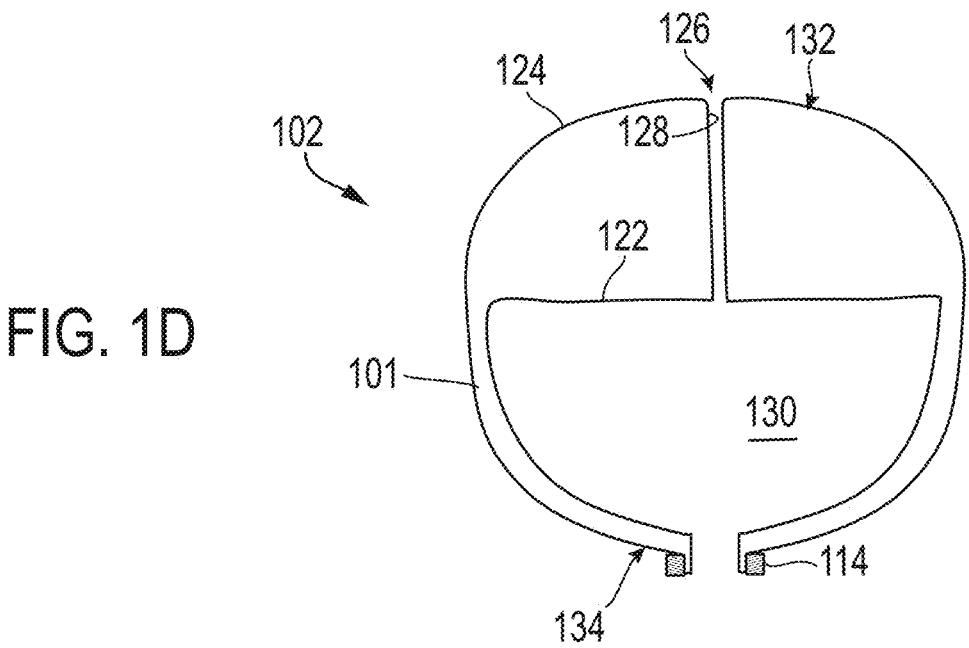
Figure 2:
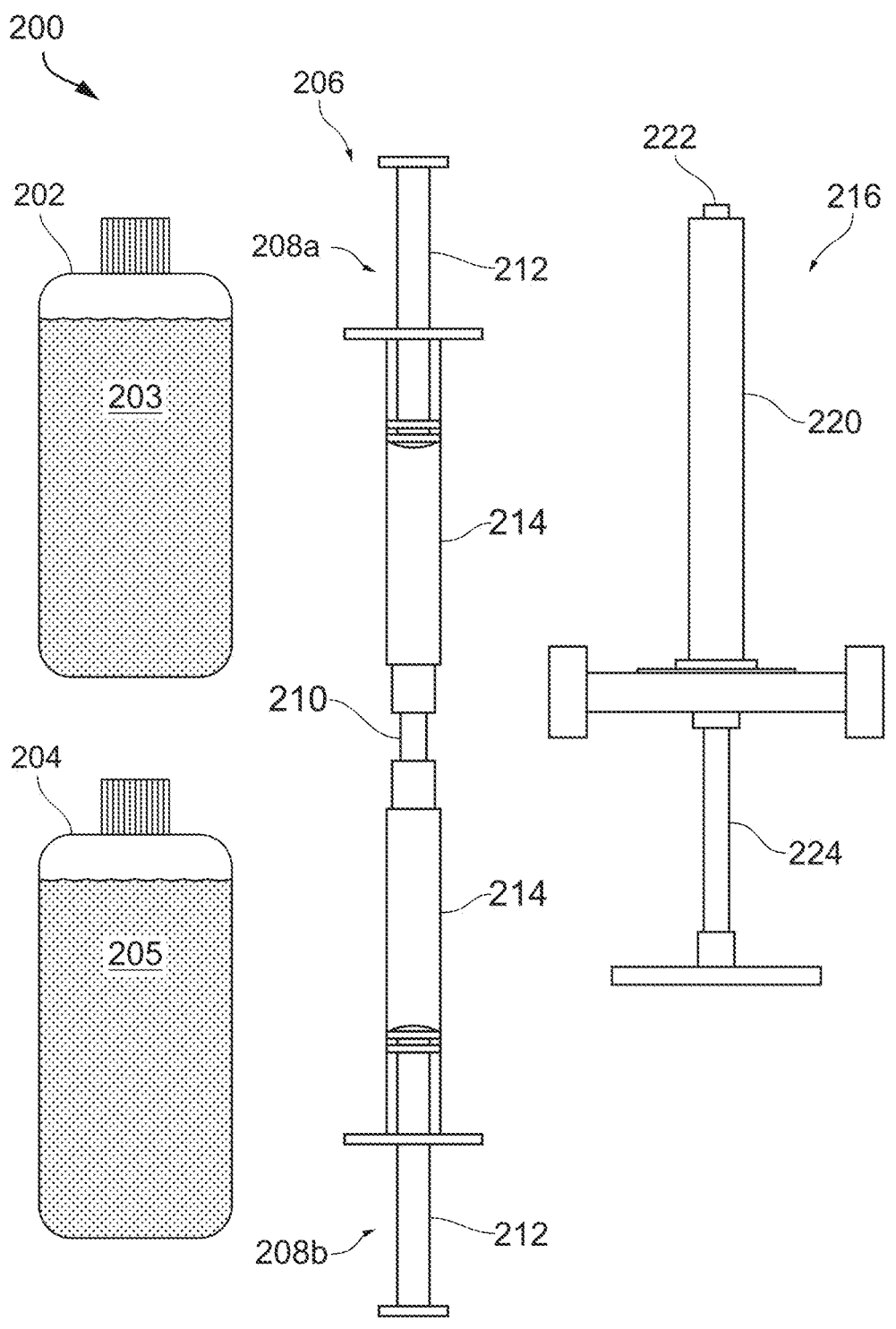
FIG. 2 shows an embolic kit according to the present technology.

In any case, the inner layer 124 may have a shape that substantially conforms to the shape of the outer layer 124, or the inner and outer layers 122, 124 may have different shapes. For example, as shown in FIG. 1D, the inner layer 122 may have a diameter or cross-sectional dimension that is less than the outer layer 124. Such a configuration may be beneficial in that the embolic element 230 experiences less resistance, at least initially, when pushing the distal wall of the occlusion member 102 downwardly towards the neck (as described in greater detail below).

In any case, both the proximal portion and the distal portion of the mesh 101 can form generally closed surfaces. However, unlike at the proximal portion of the mesh 101, the portion of the filaments at or near the fold 128 at the distal portion of the mesh 101 can move relative to one another. As such, the distal portion of the mesh 101 has both the properties of a closed end and also some properties of an open end (like a traditional stent), such as some freedom of movement of the distal-most portions of the filaments and an opening through which the conduit 116, a guidewire, guidetube, or other elongated member may pass through.

In some embodiments, each of the plurality of filaments have a first end positioned at the proximal portion of the mesh 101 and a second end also positioned at the proximal portion of the mesh 101. Each of the filaments may extend from its corresponding first end distally along the body of the mesh 101 to the fold 128, invert, then extend proximally along the mesh body to its corresponding second end at the proximal portion of the mesh 101. As such, each of the plurality of filaments have a first length that forms the inner layer 122 of the mesh 101, a second length that forms the outer layer 124 of the mesh 101, and both first and second ends fixed at the proximal portion of the mesh 101. In some embodiments, the occlusive member 102 may comprise a mesh formed of a single layer, or a mesh formed of three or more layers.

In some embodiments, the distal end surface of the mesh 101 is completely closed (i.e., does not include an aperture). In some embodiments the filaments are fixed relative to the at both the proximal and distal ends of the occlusive member 102.

The mesh 101 may be formed of metal wires, polymer wires, or both, and the wires may have shape memory and/or superelastic properties. The mesh 101 may be formed of 24, 32, 36, 48, 64, 72, 96, 128, or 144 filaments. The mesh 101 may be formed of a range of filament or wire sizes, such as wires having a diameter of from about 0.0004 inches to about 0.0020 inches, or of from about 0.0009 inches to about 0.0012 inches. In some embodiments, each of the wires or filaments have a diameter of about 0.0004 inches, about 0.0005 inches, about 0.0006 inches, about 0.0007 inches, about 0.0008 inches, about 0.0009 inches, about 0.001 inches, about 0.0011 inches, about 0.0012 inches, about 0.0013 inches, about 0.0014 inches, about 0.0015 inches, about 0.0016 inches, about 0.0017 inches, about 0.0018 inches, about 0.0019 inches, or about 0.0020 inches. In some embodiments, all of the filaments of the braided mesh 101 may have the same diameter. For example, in some embodiments, all of the filaments have a diameter of about 0.001 inches. In some embodiments, some of the filaments may have different cross-sectional diameters. For example, some of the filaments may have a slightly thicker diameter to impart additional strength to the braided layers. In some embodiments, some of the filaments can have a diameter of about 0.001 inches, and some of the filaments can have a diameter of greater than 0.001 inches. The thicker filaments may impart greater strength to the braid without significantly increasing the device delivery profile, with the thinner wires offering some strength while filling-out the braid matrix density.

The occlusive member 102 can have different shapes and sizes in an expanded, unconstrained state. For example, the occlusive member 102 may have a bullet shape, a barrel-shape, an egg shape, a dreidel shape, a bowl shape, a disc shape, a cylindrical or substantially cylindrical shape, a barrel shape, a chalice shape, etc.

B. Selected Examples of Embolic Kits

The embolic kit 200 may include one or more precursors for creation of a liquid embolic. For example, the embolic kit 200 may include a first container 202 containing a first precursor material 203 (shown schematically), a second container 204 containing a second precursor material 205 (also shown schematically), and a mixing device 206 suitable for mixing the first and second precursor materials 203, 205. The mixing device 206 can include mixing syringes 208 (individually identified as mixing syringes 208a, 208b) and a coupler 210 extending between respective exit ports (not shown) of the mixing syringes 208. The mixing syringes 208a, 208b each include a plunger 212 and a barrel 214 in which the plunger 212 is slidably received.

The embolic kit 200 can further include an injection syringe 216 configured to receive a mixture of the first and second precursor materials 203, 205 and deliver the mixture to a proximal portion 100b of the treatment assembly 100. The injection syringe 216 can include a barrel 220, an exit port 222 at one end of the barrel 220, and a plunger 224 slidably received within the barrel 220 via an opposite end of the barrel 220. The handle 103 of the treatment system 100 may have a coupler configured to form a secure fluidic connection between the lumen and the exit port 222 of the injection syringe 216.

The first and second precursor materials 203, 205 can include a biopolymer and a chemical crosslinking agent, respectively. The chemical crosslinking agent can be selected to form covalent crosslinks between chains of the biopolymer. In some embodiments, the biopolymer of the first precursor material 203 includes chitosan or a derivative or analog thereof, and the chemical crosslinking agent of the second precursor material 205 includes genipin or a derivative or analog thereof. Other suitable crosslinking agents for use with chitosan include glutaraldehyde, functionalized polyethylene glycol, and derivatives and analogs thereof. In other embodiments, the biopolymer of the first precursor material 203 can include collagen or a derivative or analog thereof, and the chemical crosslinking agent of the second precursor material 205 can include hexamethylene diisocyanate or a derivative or analog thereof. Alternatively or in addition, genipin or a derivative or analog thereof can be used as a chemical crosslinking agent for a collagen-based biopolymer. In still other embodiments, the biopolymer of the first precursor material 203 and the chemical crosslinking agent of the second precursor material 205 can include other suitable compounds alone or in combination.

Mixing the biopolymer of the first precursor material 203 and the chemical crosslinking agent of the second precursor material 205 can initiate chemical crosslinking of the biopolymer. After the first and second precursor materials 203, 205 are mixed, chemical crosslinking of the biopolymer occurs for enough time to allow the resulting embolic element 230 be delivered to the aneurysm before becoming too viscous to move through the lumen of the conduit 116. In addition, the period of time during which chemical crosslinking of the biopolymer occurs can be short enough to reach a target deployed viscosity within a reasonable time (e.g., in the range of 10-60 minutes; or at most 40 minutes, 30 minutes, 20 minutes, or 10 minutes) after delivery. The target deployed viscosity can be high enough to cause an agglomeration of the embolic element 230 to remain within the internal volume of the aneurysm without reinforcing the neck.

In at least some cases, the biopolymer has a non-zero degree of chemical crosslinking within the first precursor material 203 before mixing with the chemical crosslinking agent. This can be useful, for example, to customize the curing window for the embolic element 230 so that it corresponds well with an expected amount of time needed to deliver the material to the aneurysm. The degree of chemical crosslinking of the biopolymer within the first precursor material 203 before mixing with the chemical crosslinking agent, the ratio of the biopolymer to the chemical crosslinking agent, and/or one or more other variables can be selected to cause the embolic element 230 to have a viscosity suitable for delivery to the aneurysm via the lumen of the conduit 116 for a suitable period of time (e.g., a period within a range from 10 minutes to 40 minutes) after mixing of the first and second precursor materials 203, 205. In at least some cases, the first and second precursor materials 203, 205 are mixed in proportions that cause a weight ratio of the biopolymer to the chemical crosslinking agent in the resulting embolic element 230 to be within a range from 10:1 to 100:1, such as from 10:1 to 30:1, or from 15:1 to 50:1, or from 15:1 to 25:1. In a particular example, the first and second precursor materials 203, 205 are mixed in proportions that cause a weight ratio of the biopolymer to the chemical crosslinking agent in the resulting embolic element 230 to be 30:1.

Use of a biopolymer instead of an artificial polymer in the first precursor material 203 may be advantageous because biopolymers tend to be more readily bioabsorbed than artificial polymers and/or for other reasons. Furthermore, use of a chemical crosslinking agent instead of a physical crosslinking agent (i.e., a crosslinking agent that forms noncovalent crosslinks between chains of the biopolymer) in the second precursor material 205 may be advantageous because chemically crosslinked polymers tend to be more cohesive than physically crosslinked polymers and/or for other reasons. In the context of forming a tissue scaffold within an aneurysm, high cohesiveness of the embolic element 230 may be more important than it is in other contexts to secure the cured embolic element 230 within the aneurysm 302. For example, high cohesiveness of the embolic element 230 may reduce or eliminate the possibility of a piece of the embolic element 230 breaking free and entering a patient's intracerebral blood stream during delivery.

The first and second precursor materials 203, 205 may include other components and/or the kit 200 may include other precursor materials intended for mixing with the first and second precursor materials 203, 205. For example, the first, second, and/or another precursor material may include a physical crosslinking agent. The presence of a physical crosslinking agent may be useful to form physical crosslinks that complement chemical crosslinks from the chemical crosslinking agent. The combination of chemical and physical crosslinks may enhance the cohesiveness of the embolic element 230. Suitable physical crosslinking agents for use with chitosan-based biopolymers include β glycerophosphate, mannitol, glucose, and derivatives and analogs thereof. In these and other cases, the embolic element 230 may include multiple chemical crosslinking agents and/or multiple physical crosslinking agents.

A contrast agent is another component that may be added to the precursor materials. The presence of a contrast agent within the embolic element 230 can be useful to visualize delivery of the embolic element 230 using fluoroscopy. One problem with using conventional platinum coils in intracranial aneurysms is that the persistent radiopacity of the coils tends to interfere with visualizing other aspects of the treatment in follow-up imaging. For example, the presence of platinum coils within an aneurysm may make it difficult or impossible to detect by fluoroscopy the presence of blood-carried contrast agent that would otherwise indicate recanalization. In at least some embodiments of the present technology, a contrast agent within the embolic element 230 is selected to provide radiopacity that diminishes over time. For example, the contrast agent may initially be radiopaque to facilitate delivery of the embolic element 230 and then become less radiopaque to facilitate follow-up imaging. In a particular example, the first, second, and/or another precursor material includes iohexol or a derivative or analog thereof as a suitable contrast agent.

In animal studies, the liquid embolics of the present technology were shown to provide (a) complete or nearly complete volumetric filling of the aneurysm internal volume, and (b) complete or nearly complete coverage of the aneurysm neck with new endothelial tissue. These features, among others, are expected to result in a lower recanalization rate than that of platinum coil treatments and faster aneurysm occlusion than that of flow diverters. Furthermore, the injectable scaffold material is expected to be bioabsorbed and thereby reduced in volume over time. Thus, unlike platinum coils, the injectable scaffold is expected to have little or no long-term mass effect. Furthermore, the injectable scaffold material can be configured to have diminishing radiopacity; therefore, when so configured it will not interfere future CT and MRI imaging and procedures. Embodiments of the present technology can have these and/or other features and advantages relative to conventional counterparts whether or not such features and advantages are described herein.

In some embodiments, the embolic kit 200 and/or embolic element 230 may be any embolic or occlusive device, such as one or more embolic coils, polymer hydrogel(s), polymer fibers, mesh devices, or combinations thereof. The embolic kit 200 may include one or more precursors that, once mixed together, form the embolic element 230 that remains within the aneurysm. In some embodiments, the embolic kit 200 may include the embolic element pre-mixed.

In some embodiments, the embolic kit 200 and/or embolic element 230 may be any embolic or occlusive device, such as one or more embolic coils, polymer hydrogel(s), polymer fibers, mesh devices, or combinations thereof. The embolic kit 200 may include one or more precursors that, once mixed together, form the embolic element 230 that remains within the aneurysm. In some embodiments, the embolic kit 200 may include the embolic element pre-mixed.

Additional details regarding suitable embolic element may be found in U.S. patent application Ser. No. 15/299, 929, filed Oct. 21, 2016, the disclosure of which is incorporated herein by reference in its entirety.

II. SELECTED METHODS FOR TREATING ANEURYSMS

FIGS. 3A-3G depict an example method for treating an aneurysm A with the systems 10 of the present technology. To begin, a physician may intravascularly advance the second elongated shaft 108 towards an intracranial aneurysm (or other treatment location such as any of those described herein) with the occlusive member 102 in a low-profile state. A distal portion of the second elongated shaft 108 may be advanced through a neck N of the aneurysm A to locate a distal opening of the second elongated shaft 108 within an interior cavity of the aneurysm A. The elongated member 106 may be advanced distally relative to the second elongated shaft 108 to push the occlusive member 102 through the opening at the distal end of the second elongated shaft 108, thereby releasing the occlusive member 102 from the shaft 108 and allowing the occlusive member 102 to self-expand into a first expanded state. Releasing the occlusive member 102 from the shaft 108 and allowing the occlusive member 102 to self-expand into a first expanded state may alternatively, or additionally, include withdrawing shaft 108 relative to the elongated member 106.

Figures 3A, 3B:
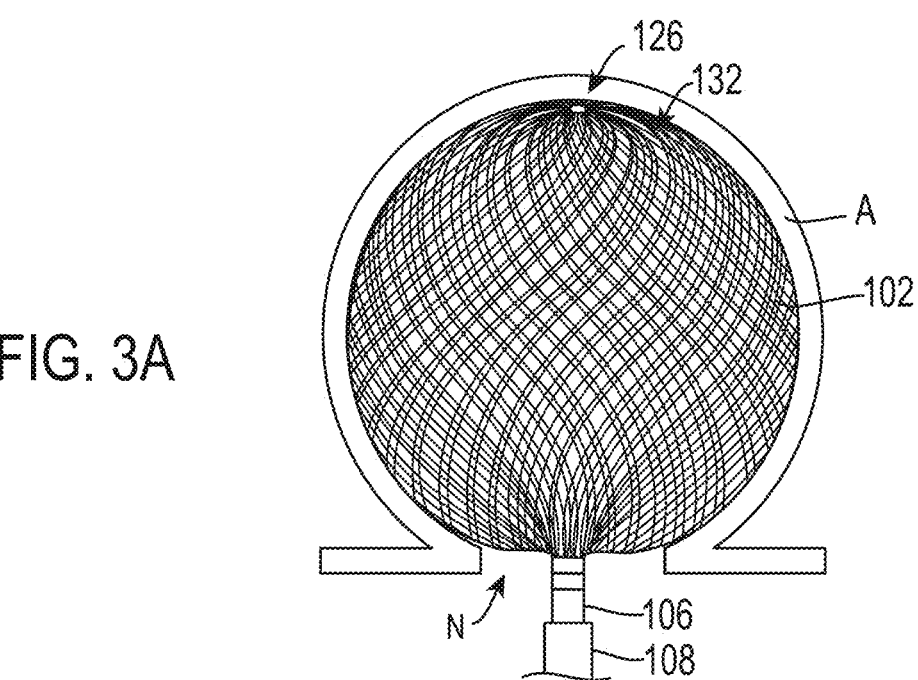
FIGS. 3A-3G depict an example method of treating an aneurysm with the treatment system of the present technology.

FIG. 3A shows the occlusive member 102 in a first expanded state, positioned in an aneurysm cavity and still coupled to the elongated member 106. As shown in FIG. 3A, in the first expanded state, the occlusive member 102 may assume a predetermined shape that encloses an internal volume 130 (see FIG. 1C). In this first expanded state, the occlusive member 102 may generally conform to the shape of the aneurysm A. As illustrated in FIG. 3B with the occlusive member 102 and delivery system shown in cross-section, the conduit 116 may be advanced through the internal volume 130 of the occlusive member 102 such that a distal opening of the conduit 116 is at or distal to the aperture 126 at the distal portion of the occlusive member 102. The embolic element 230 may be delivered through the conduit 116 to a space between the occlusive member 102 and an inner surface of the aneurysm wall W.

In some embodiments, the method includes mixing the first and second precursor materials 203, 205 (FIG. 2) to form the embolic element 230. Mixing of the first and second precursor materials 203, 205 may occur prior to introducing the embolic element 230 to the treatment system 100 and/or during delivery of the embolic element through the conduit 116 to the aneurysm. In a particular example, the first precursor material 203 is loaded into one of the barrels 214, the second precursor materials 205 is loaded into the other barrel 214, and the mixing syringes 208 are coupled via the coupler 210. To mix the first and second precursor materials 203, 205, the plungers 212 are alternately depressed, thereby causing the first and second precursor materials 203, 205 to move repeatedly from one barrel 214 to the other barrel 214. After suitably mixing the precursor materials, the resulting embolic element 230 can be loaded into the barrel 220 of the injection syringe 216. The injection syringe 216 may then be coupled to a proximal end of the conduit 116 to deliver the embolic element 230 through the conduit 116 and into the aneurysm A. As the embolic element 230 passes through the lumen of the conduit 116, chemical crosslinking of the biopolymer can continue to occur.

Figure 3C:
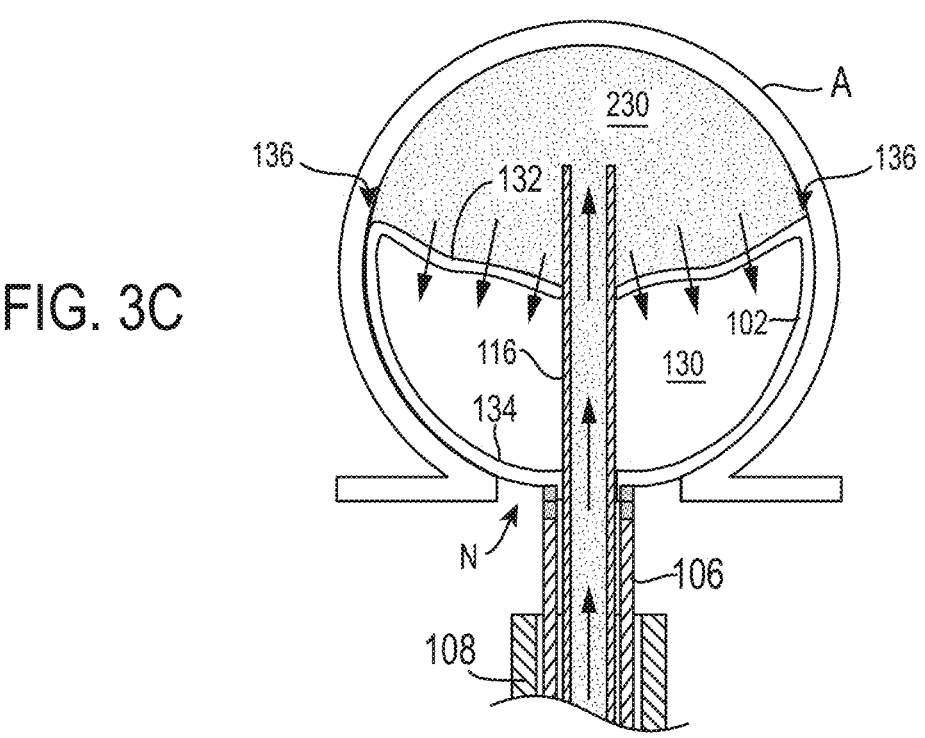
Figure 3D:
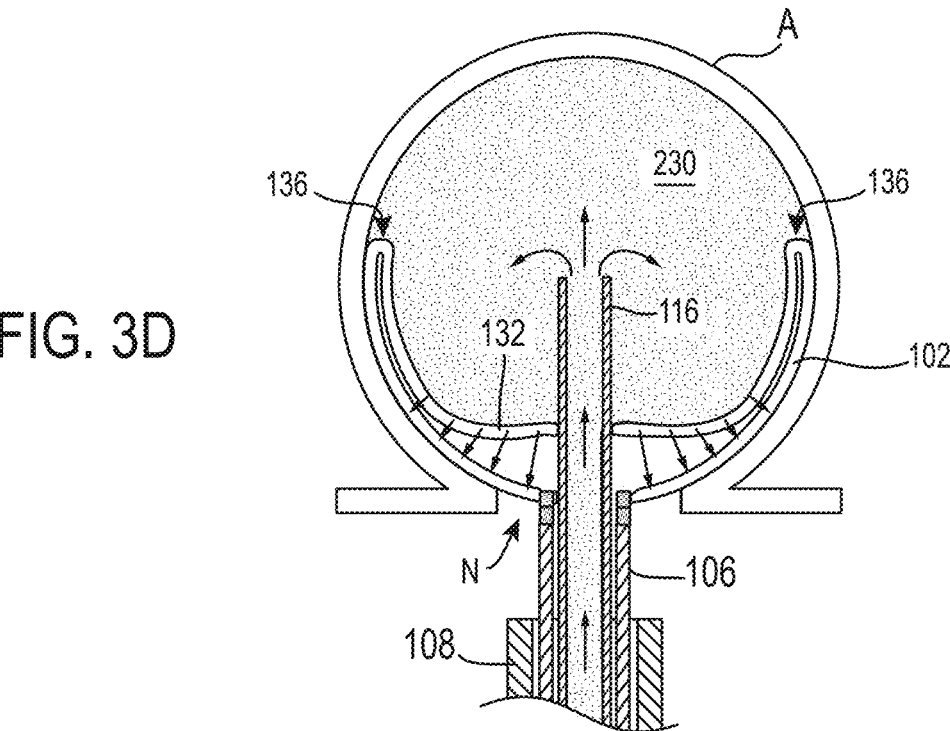

Still with reference to FIG. 3B, as the embolic element 230 is delivered between the dome of the aneurysm A and the distal portion 132 of the wall of the occlusive member 102, pressure builds between the aneurysm wall W and the occlusive member 102. As shown in the progression of FIGS. 3B-3D, when the forces on the occlusive member 102 reach a threshold level, the embolic element 230 pushes the distal wall 132 downwardly towards the neck N of the aneurysm A. The embolic element 230 exerts a substantially uniform pressure across the distal surface of the occlusive member 102 that collapses the occlusive member 102 inwardly on itself such that the rounded distal wall 132 transitions from concave towards the neck N of the aneurysm A to convex towards the neck N. The pressure and inversion of the distal portion of the wall 132 creates an annular fold 136 that defines the distal-most edge of the occlusive member 102. As the occlusive member 102 continues to invert, the position of the fold 136 moves towards the neck N, which continues until a distal-most half of the occlusive member 102 has inverted. In some embodiments, the occlusive member 102 may include one or more portions configured to preferentially flex or bend such that the occlusive member 102 folds at a desired longitude. Moreover, as the occlusive member 102 collapses, a distance between the wall at the distal portion 132 and the wall at the proximal portion decreases, and thus the internal volume 130 of the occlusive member 102 also decreases. As the occlusive member 102 collapses, the conduit 116 may be held stationary, advanced distally, and/or retracted proximally.

During and after delivery of the embolic element 230, none or substantially none of the embolic element 230 migrates through the pores of the occlusive member 102 and into the internal volume 130. Said another way, all or substantially all of the embolic element 230 remains at the exterior surface or outside of the occlusive member 102. Compression of the occlusive member with the embolic element 230 provides a real-time "leveling" or "aneurysm-filling indicator" to the physician under single plane imaging methods (such as fluoroscopy) so that the physician can confirm at what point the volume of the aneurysm is completely filled. It is beneficial to fill as much space in the aneurysm as possible, as leaving voids within the aneurysm sac may cause delayed healing and increased risk of aneurysm recanalization and/or rupture. While the scaffolding provided by the occlusive member 102 across the neck helps thrombosis of blood in any gaps and healing at the neck, the substantial filling of the cavity prevents rupture acutely and does not rely on the neck scaffold (i.e., the occlusive member 102). Confirmation of complete or substantially complete aneurysm filling under single plane imaging cannot be provided by conventional devices.

Once delivery of the embolic element 230 is complete, the conduit 116 may be withdrawn. In some embodiments, the embolic element 230 may fill greater than 40% of the aneurysm sac volume. In some embodiments, the embolic element 230 may fill greater than 50% of the aneurysm sac volume. In some embodiments, the embolic element 230 may fill greater than 60% of the aneurysm sac volume. In some embodiments, the embolic element may fill greater than 65%, 70%, 75%, 80%, 85%, or 90% of the aneurysm sac volume.

Figure 3E:
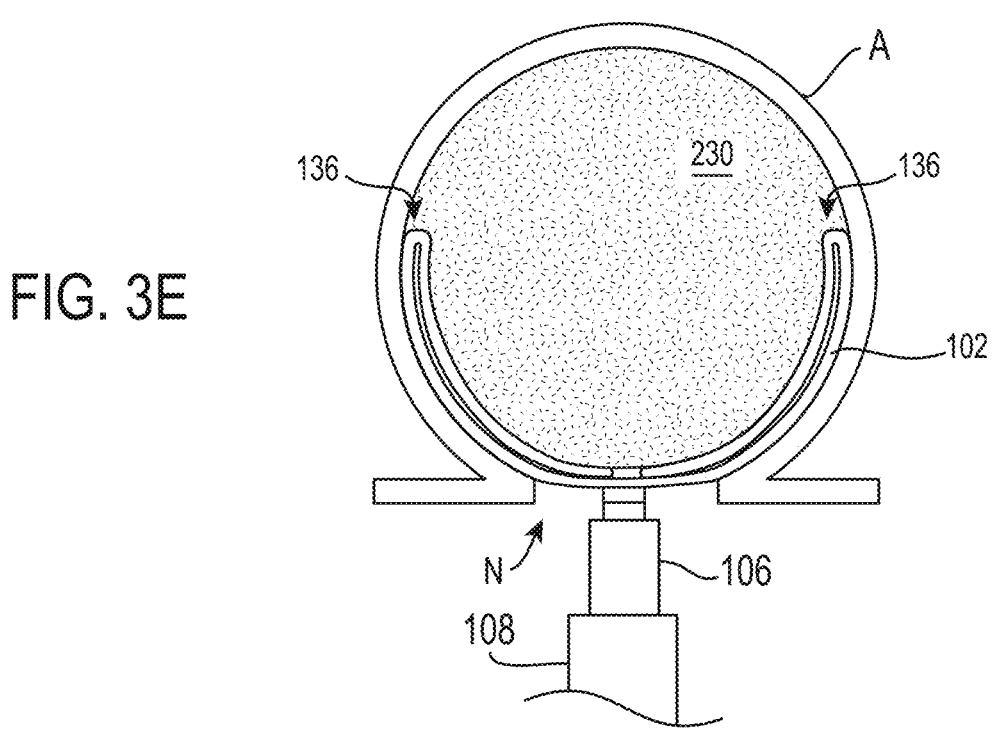
Figure 3F:
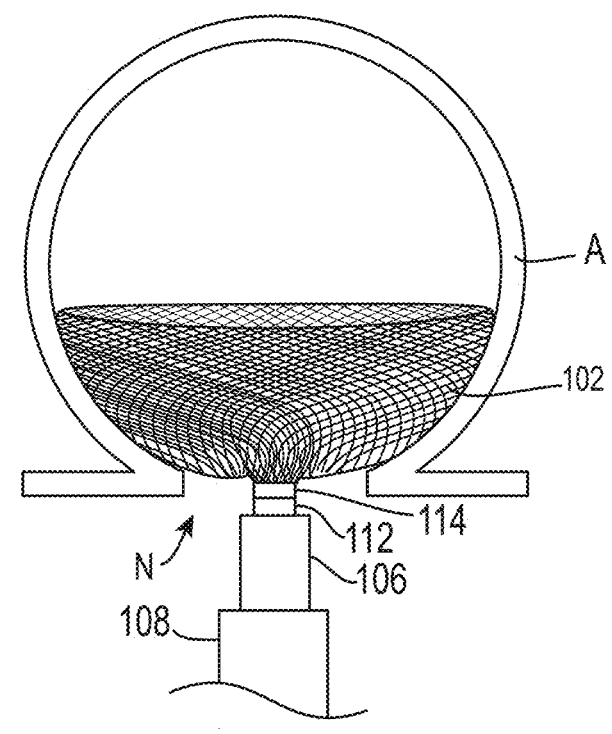

FIG. 3E shows a second expanded state of the occlusive member 102, shown in cross-section, with the embolic element 230 occupying the remaining volume of the aneurysm A. FIG. 3F shows the occlusive member 102 in full with the embolic element 230 removed so the second shape of the occlusive member 102 is visible. As shown, the embolic element 230 may be delivered until the occlusive member 102 is fully-collapsed such that the occlusive member 102 has substantially no internal volume.

In the second expanded state, the occlusive member 102 may form a bowl shape that extends across the neck of the aneurysm A. The wall of the occlusive member 102 at the distal portion may now be positioned in contact with or immediately adjacent the wall of the occlusive member 102 at the proximal portion. The distal wall 132 may be in contact with the proximal wall 134 along all or substantially all of its length. In some embodiments, the distal wall 132 may be in contact with the proximal wall 134 along only a portion of its length, while the remainder of the length of the distal wall 132 is in close proximity—but not in contact with—the proximal wall 134.

Collapse of the occlusive member 102 onto itself, towards the neck N of the aneurysm, may be especially beneficial as it doubles the number of layers across the neck and thus increases occlusion at the neck N. For example, the distal wall 132 collapsing or inverting onto the proximal wall 134 may decrease the porosity of the occlusive member 102 at the neck N. In those embodiments where the occlusive member 102 is a mesh or braided device such that the distal wall 132 has a first porosity and the proximal wall 134 has a second porosity, deformation of the distal wall 132 onto or into close proximity within the proximal wall 134 decreases the effective porosity of the occlusive member 102 over the neck N. The resulting multi-layer structure thus has a lower porosity than the individual first and second porosities. Moreover, the embolic element 230 along the distal wall 132 provides additional occlusion. In some embodiments, the embolic element 230 completely or substantially completely occludes the pores of the adjacent layer or wall of the occlusion member 102 such that blood cannot flow past the embolic element 230 into the aneurysm cavity. It is desirable to occlude as much of the aneurysm as possible, as leaving voids of gaps can allow blood to flow in and/or pool, which may continue to stretch out the walls of aneurysm A. Dilation of the aneurysm A can lead to recanalization and/or herniation of the occlusive member 102 and/or embolic element 230 into the parent vessel and/or may cause the aneurysm A to rupture. Both conditions can be fatal to the patient.

In those embodiments where the wall of the occlusive member 102 comprises an inner and outer layer, the deformed or second shape of the occlusive member 102 forms four layers over the neck N of the aneurysm A In those embodiments where the wall of the occlusive member 102 comprises a single layer, the deformed or second shape of the occlusive member 102 forms two layers over the neck N of the aneurysm A As previously mentioned, the neck coverage provided by the doubled layers provides additional surface area for endothelial cell growth, decreases the porosity of the occlusive member 102 at the neck N (as compared to two layers or one layer), and prevents herniation of the embolic element 230 into the parent vessel. During and after delivery, the embolic element 230 exerts a substantially uniform pressure on the occlusive member 102 towards the neck N of the aneurysm A, thereby pressing the portions of the occlusive member 102 positioned adjacent the neck against the inner surface of the aneurysm wall such that the occlusive member 102 forms a complete and stable seal at the neck N.

Figure 3G:
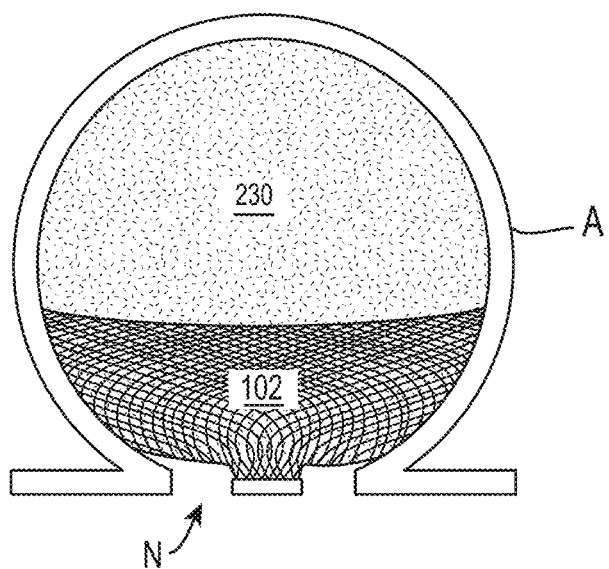

As shown in FIG. 3G, the first coupler 112 may be detached from the second coupler 114 and the elongated member 106 and second elongated shaft 108 may be withdrawn, thereby leaving the occlusive member 102 and embolic element 230 implanted within the aneurysm A. For example, the occlusive member 102 may be detached from the elongated member 106 using any of the electrolytic detachment mechanisms described in more detail below.

Over time natural vascular remodeling mechanisms and/or bioabsorption of the embolic element 230 may lead to formation of a thrombus and/or conversion of entrapped thrombus to fibrous tissue within the internal volume of the aneurysm A. These mechanisms also may lead to cell death at a wall of the aneurysm and growth of new endothelial cells between and over the filaments or struts of the occlusive member 102. Eventually, the thrombus and the cells at the wall of the aneurysm may fully degrade, leaving behind a successfully remodeled region of the blood vessel.

In some embodiments, contrast agent can be delivered during advancement of the occlusive member 102 and/or embolic element 230 in the vasculature, deployment of the occlusive member 102 and/or embolic element 230 at the aneurysm A, and/or after deployment of the occlusive member 102 and/or embolic element 230 prior to initiation of withdrawal of the delivery system. The contrast agent can be delivered through the second elongated shaft 108, the conduit 116, or through another catheter or device commonly used to delivery contrast agent. The aneurysm (and devices therein) may be imaged before, during, and/or after injection of the contrast agent, and the images may be compared to confirm a degree of occlusion of the aneurysm.

According to some aspects of the technology, the system 10 may comprise separate first and second elongated shafts (e.g., microcatheters) (not shown), the first dedicated to delivery of the embolic element, and the second dedicated to the delivery of the occlusive member. In example methods of treating an aneurysm, the first elongated shaft may be intravascularly advanced to the aneurysm and through the neck such that that a distal tip of the first elongated shaft is positioned within the aneurysm cavity. In some embodiments, the first elongated shaft may be positioned within the aneurysm cavity such that the distal tip of the shaft is near the dome of the aneurysm.

The second elongated shaft containing the occlusive member (such as occlusive member 102) may be intravascularly advanced to the aneurysm and positioned within the aneurysm cavity adjacent the first elongated shaft. The occlusive member may then be deployed within the aneurysm sac. As the occlusive member is deployed, it pushes the first elongated shaft outwardly towards the side of the aneurysm, and when fully deployed the occlusive member holds or "jails" the first elongated shaft between an outer surface of the occlusive member and the inner surface of the aneurysm wall.

The embolic element (such as embolic element 230) may then be delivered through the first elongated shaft to a position between the inner surface of the aneurysm wall and the outer surface of the occlusive member. For this reason, it may be beneficial to initially position the distal tip of the first elongated shaft near the dome (or more distal surface) of the aneurysm wall. This way, the "jailed" first elongated shaft will be secured by the occlusive member such that the embolic element gradually fills the open space in the aneurysm sac between the dome and the occlusive member. As described elsewhere herein, the filling of the embolic element pushes and compresses the occlusive member against the tissue surrounding the aneurysm neck as the space in the sac above the occlusive member is being filled from the dome to the neck. Also as described elsewhere herein, the compression of the occlusive member with the embolic element provides a "leveling or aneurysm filling indicator" which is not provided by conventional single plane imaging methods. The filling of the embolic element may complete, for example, when it occupies about 50-80% of the volume of the aneurysm.

III. EXAMPLE SYSTEMS WITH ELECTROLYTIC DETACHMENT MECHANISMS

Figures 4A, 4B:
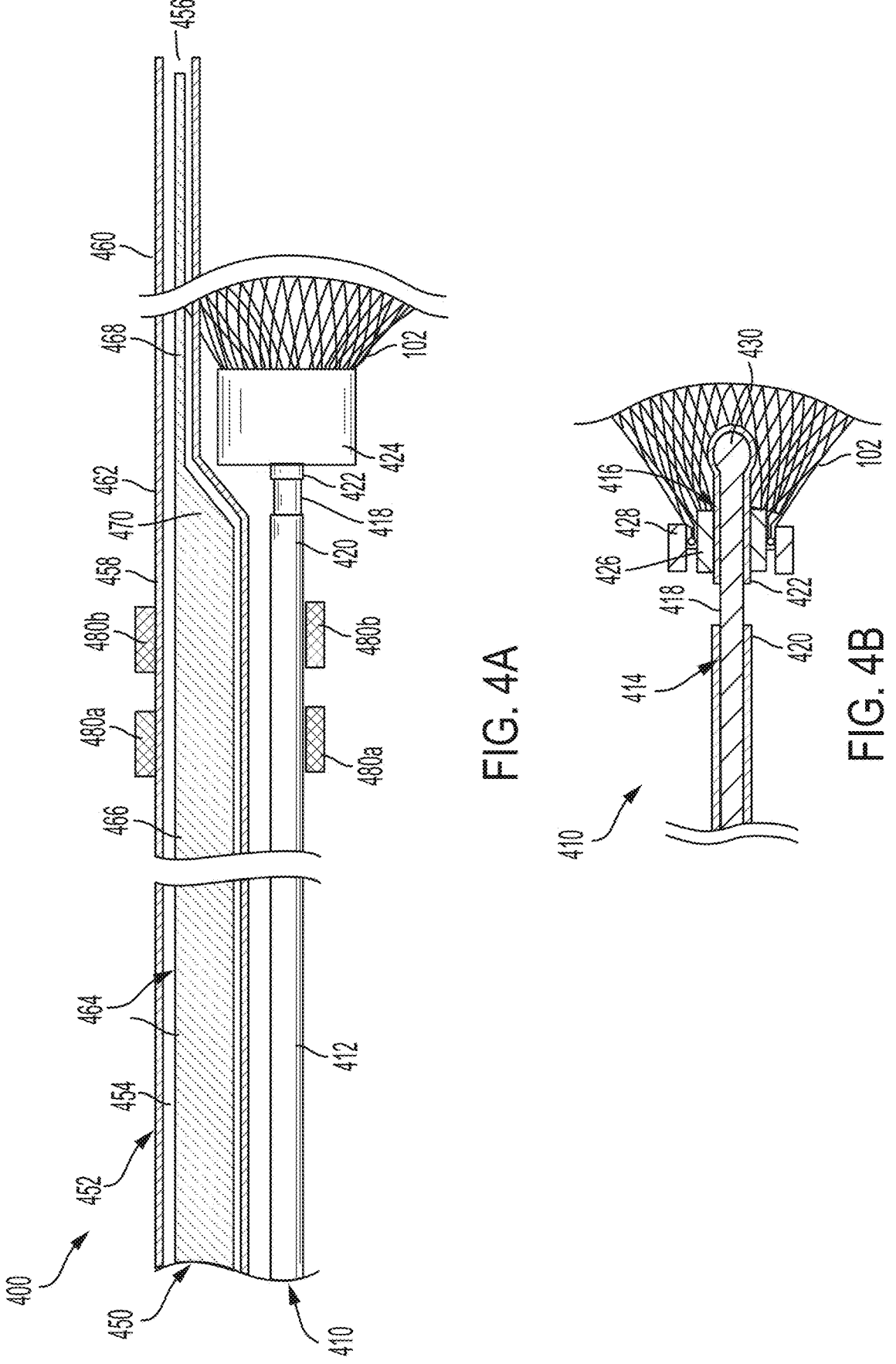
FIG. 4A shows a schematic side view of a treatment system in accordance with aspects of the present technology.
FIG. 4B shows a schematic side cross-sectional view of a portion of the treatment system of FIG. 4A.

FIG. 4A shows a schematic side view of a treatment system 400, and FIG. 4B shows a side cross-sectional view of a distal portion of the treatment system 400 shown in FIG. 4A, with the occlusive member delivery assembly omitted for clarity. As described in more detail below, the treatment system 400 can include an occlusive member delivery assembly 410 and an embolic element delivery assembly 450, which can be coupled together via one or more couplers 480. In operation, the occlusive member delivery assembly 410 facilitates placement of the occlusive member 102 at the treatment site and utilizes electrolytic detachment to release the occlusive member 102 from its delivery assembly 410. The embolic element delivery assembly 450, which can extend adjacent and generally parallel to the occlusive member delivery assembly 410 along some or all of its length, can facilitate introduction of an embolic element 230 (FIGS. 2-3G) therethrough for placement at the treatment site.

The occlusive member delivery assembly 410 includes the occlusive member 102 coupled to a distal end of the elongated member 106. In some embodiments, the elongated member 106 can take the form of an electrolytically corrodible core wire 412, which may be monolithic or composed of multiple separate components joined together. According to some embodiments, as shown in FIGS. 4A and 4B, the electrolytically corrodible core wire 412 includes a proximal portion 414, a distal portion 416, and a detachment zone 418 disposed between the proximal portion 414 and the distal portion 416. At least a portion of the core wire 412, including the detachment zone 418, can be coated with a conductive material, such as carbon, gold, platinum, tantalum, combinations thereof, and the like. One or more metallic coatings can be applied using known plating techniques.

The core wire 412, including the detachment zone 418, can include one or more of the following materials: ceramic materials, plastics, base metals or alloys thereof, and preferably stainless steel. Some of the most suitable material combinations for forming the electrolytically corrodible points can include one or more of the following: stainless steels, preferably of the type AISI 301,304, 316, or subgroups thereof; Ti or TiNi alloys; Co-based alloys; noble metals; or noble metal alloys, such as Pt, Pt metals, Pt alloys, Au alloys, or Sn alloys. Further, ceramic materials and plastics employed for forming the medical device can be electrically conductive.

According to some embodiments, portions of the core wire 412 can be coated with a nonconductive material. A proximal insulating layer 420 can be provided over at least a portion of an outer surface of the proximal portion 414 of the core wire 412. For example, the proximal insulating layer 420 can circumferentially surround an outer surface of the proximal portion 414. A distal insulating layer 422 can be provided over at least a portion of an outer surface of the distal portion 416 of the core wire 412. For example, the distal insulating layer 422 can circumferentially surround and contact an outer surface of the distal portion 416. The proximal and distal insulating layers 420, 422, can be of an electrically nonconductive or insulative polymer, such as polyimide, polypropylene, polyolefins, combinations thereof, and the like.

According to some embodiments, proximal and distal insulating layers 420, 422 leave exposed the detachment zone 418 of the core wire 412. When in contact with a body fluid, such as blood, the fluid serves as an electrolyte allowing current to be focused on the non-coated detachment zone 418. The proximal and distal insulating layers 420, 422 prevent exposure of the proximal portion 414 and distal portion 416 to the fluid. Accordingly, electrical energy conducted along the core wire 412 is concentrated at the detachment zone 418, thereby reducing the time required to erode away the detachment zone 418. The proximal and distal insulating layers 420, 422 can be over-molded, co-extruded, sprayed on, or dip-coated with respect to the core wire 412.

Laser ablation can be employed to selectively remove the coating to a controlled length minimizing the time required to erode through the component. Lengths as small as 0.0005" and as large as 0.1" or longer can be removed. According to some embodiments, lengths of detachment zone 418 can be greater than 0.005" and/or less than 0.010" to provide sufficient exposure to achieve detachment times of less than 30 seconds. In some embodiments, the detachment zone 418 can have a smaller cross-sectional profile or outer diameter than the proximal and/or distal portions 414, 416. In some embodiments, the detachment zone 418 can include additional or alternative materials to facilitate electrolytic corrosion at this zone.

According to some embodiments, the distal insulating layer 422 is disposed radially between the distal portion 416 of the core wire 412 and the hub 424 of the occlusive member 102. As shown in FIG. 4B, an inner band 426 of the hub 424 circumferentially surrounds and contacts the distal insulating layer 422. An outer band 428 surrounds the inner band 426, such that proximal portions of the layers of the occlusive member 102 are grasped between the inner and outer bands 426, 428 of the hub 424.

As shown in FIG. 4B, the distal insulating layer 422 electrically isolates the occlusive member 102 from an electrical charge conducted along a length of the core wire 412. A proximal end of the distal insulating layer 422 may be positioned proximal to the hub 424, and a distal end of the distal insulating layer 422 may be positioned distal to the hub 424. Likewise, a proximal end of the distal portion 416 may be positioned proximal to the hub 424, and a distal end of the distal portion 416 may be positioned distal to the hub 424, such that the distal portion 416 extends through and distally beyond a lumen formed by the hub 424.

The core wire 412 can include an anchor end 430 at a terminal distal end of the core wire 412. The anchor end 430 can be located distal to the hub 424. For example, the anchor end 430 can be located within an interior portion of the occlusive member 102. The anchor end 430 can have a maximum cross-sectional dimension that is greater than an inner cross-sectional dimension of the inner band 426. Accordingly, the core wire 412 is prevented from moving proximally entirely through the inner band 426. For example, an interface between the distal insulating layer 422 and the inner band 426 or an interface between the distal insulating layer 422 and the core wire 412 may allow a degree of movement of the core wire 412 relative to the inner band 426. To prevent the core wire 412 from being removed distally from within the inner band 426, the anchor end 27 can be of a size that cannot pass entirely proximally through the inner band 426.

Alternatively, the proximal end of the distal insulating layer 422 may be coterminous with a proximal end of the hub 424, and/or a distal end of the distal insulating layer 422 may be coterminous with a distal end of the hub 424. Likewise, the proximal end of the distal portion 416 may be coterminous with a proximal end of the hub 424, and/or a distal end of the distal portion 416 may be coterminous with a distal end of the hub 424.

According to some embodiments, a detachment zone 418 can be configured such that the corrodible portion thereof defines a unique structure configured to enhance electrolytic corrosion while preserving the structural characteristics thereof, A reduction in corrosion resistance will reduce a time required to deploy an intravascular and/or intrasaccular implant, thus reducing the overall procedure time. According to some embodiments, corrosion resistance of detachment zone 418 is decreased by exposure to laser or other energy, causing the detachment zone 418 to be structurally modified by heat. As a result, the detachment zone 418 will have a different microstructure than the material outside of the zone (e.g., the proximal portion 414 and/or the distal portion 416 of the core wire 412). The result will decrease the time to electrolytically plate off the material, resulting in faster detachment times.

The laser energy will create surface defects for a reduction in corrosion resistance. The laser energy will also alter the microstructure at a specific area, leading to a non-uniform corrosion rate. Accordingly, the preferred corrosion site can have a faster detach time. According to some embodiments, the proximal portion 414 and/or the distal portion 416 have a microstructure with a crystallinity that is greater than a crystallinity of a microstructure of the detachment zone 418. According to some embodiments, the detachment zone 418 comprises a microstructure that is more amorphous than each of (i) a microstructure of the proximal portion 414 and (ii) a microstructure of the distal portion 416. According to some embodiments, a method of treating includes providing an electrolytically corrodible core wire 412 comprising a proximal portion 414, a distal portion 416, and a detachment zone 418 between the proximal portion 414 and the distal portion 416. The detachment zone 418 is treated to produce a microstructure in the detachment zone 418 that is more amorphous than each of (i) a microstructure of the proximal portion 414 and (ii) a microstructure of the distal portion 416.

A shown in FIG. 4A, the embolic element delivery assembly 450 can extend adjacent to the occlusive member delivery assembly 410. In some embodiments, the embolic element delivery assembly 450 includes a conduit 452 defining a lumen 454 extending therethrough. The lumen 454 can terminate in a distal opening 456. In some embodiments, the conduit 452 can be an elongate flexible tubular member, for example a catheter, hypotube, polymer tube, etc. The lumen 454 can be coated with a lubricious material or lining to facilitate advancement of embolic element(s) therethrough. In some embodiments, the conduit 452 is dimensioned such that the distal opening 456 is disposed adjacent to, completely distal of, or at least partially distal of the occlusive member 102 while the occlusive member 102 is in the unexpanded state. In some embodiments, the conduit 452 can be dimensioned and configured such that the distal opening 456 is disposed at distal to the hub 424 of the occlusive member 102, such that embolic element(s) delivered therethrough can be delivered to a region adjacent or distal of the occlusive member 102.

As seen in FIG. 4A, the conduit 452 and its lumen 454 can each have a cross-sectional dimension that varies along the length of the conduit 452. For example, the conduit 452 can include a proximal portion 458, a distal portion 460, and a transition portion 462 between the proximal and distal portions 458, 460. In some embodiments, the proximal portion 458 has a larger cross-sectional dimension than the distal portion 460, and the transition portion 462 can have a tapered profile or diameter. In some embodiments, the transition portion 462 can include one or more steps or abrupt transitions instead of or in addition to any gradual tapering transitions. In the illustrated embodiment, the wall thickness of the conduit 452 is substantially uniform, such that the conduit 452 and the lumen 454 step down in cross-sectional dimension in tandem. In some embodiments, the wall thickness may vary, for example such that while the outer cross-sectional dimension of the conduit 452 steps down according to a first profile, the lumen 454 steps down according to a different profile (e.g., with a more or less gradual taper), or in some instances the lumen 454 may be substantially uniform along its length. In still other embodiments, the conduit 452 can have a substantially constant diameter along its length, or may gradually taper over substantially its entire length.

A stylet 464 can be sized and configured to be slidably received within the lumen 454 of the conduit 452. In operation, the stylet 464 can provide increased rigidity to enhance pushability of the conduit 452, which may otherwise be too flexible to permit pushability through a surrounding guide catheter. In various embodiments, the stylet 464 can be metallic, polymeric, rubber, or any other suitable material. In some embodiments, the stylet 464 is generally stiffer than the conduit 452. As seen in FIG. 4A, the stylet 464 can have an outer cross-sectional dimension that substantially corresponds to the lumen 454 of the conduit 452, for example having a proximal portion 466, a distal portion 468, and a transition portion 470 therebetween. Alternatively, the stylet 464 may have a constant cross-sectional dimension.

As noted previously, the occlusive member delivery assembly 410 and the embolic element delivery assembly 450 can be coupled together via one or more couplers 480. In the embodiment shown in FIG. 4A, the couplers include a first coupler 480a and a second coupler 480b. The couplers 480 can be loops or bands that extend circumferentially around both the conduit 452 and the core wire 412 to secure them together. Such bands can be made of any suitable material, for example being polymeric or metallic, and optionally may be radiopaque to facilitate visualization of the system 400 as it advanced through the vasculature. The bands can be crimped over the assemblies 410, 450, with or without an adhesive or weld to secure them in place. Although two such couplers 480 are shown, the number of couplers can vary, for example one, three, four, five, or more couplers can be used to secure the conduit 452 and the core wire 412 together. In some embodiments, the coupler 480 can take the form of an adhesive that fastens at least a portion of the core wire 412 to at least a portion of the conduit 452. In some embodiments, the coupler 480 can include a surrounding sheath, for example a polymeric material that can surround the conduit 452 and the core wire 412 to securely hold them together, for example being heat-shrunk or otherwise snugly fit over the conduit 452 and the core wire 412. In various embodiments, the occlusive member delivery assembly 410 and the embolic element delivery assembly 450 can be coupled together such that the two are not slidable or rotatable relative to one another. In other embodiments, the two assemblies 410, 450 can be slidably coupled together, such that the embolic element delivery assembly 450 can be slidably advanced or retracted with respect to the occlusive member delivery assembly 410. In other embodiments, the two assemblies 410, 450 may be uncoupled, such that each can be separately advanced to the treatment site simultaneously or sequentially.

Figures 5A, 5B, 5C:
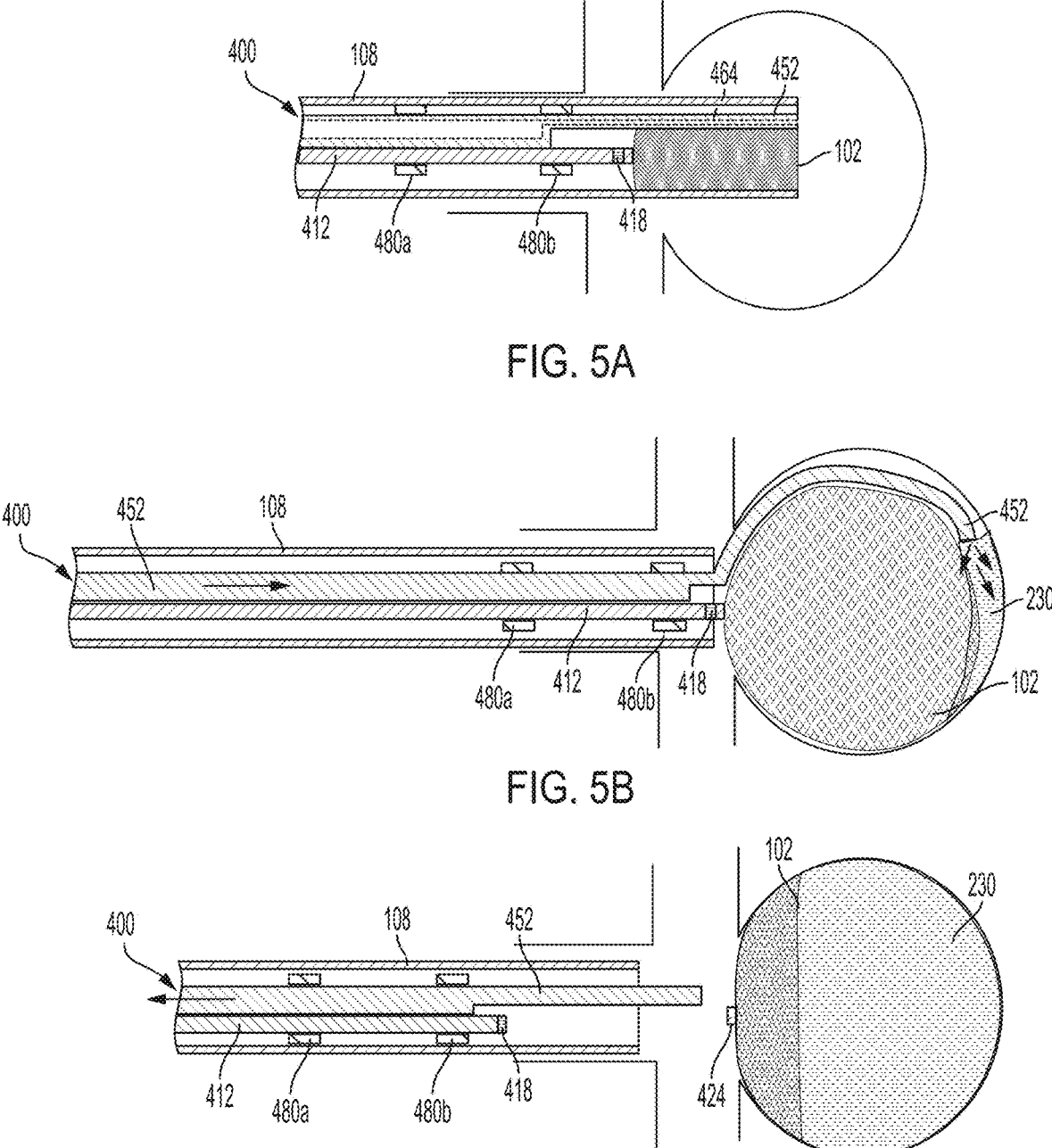
FIGS. 5A-5C illustrate delivery of an occlusive member and embolic element to a treatment site in accordance with aspects of the present technology.

FIGS. 5A-5C illustrate delivery of an occlusive member 102 and embolic element 230 to a treatment site within an aneurysm sac. As shown in FIG. 5A, the system 400 can be positioned within a second elongate shaft 108 (e.g., a microcatheter) for intravascular advancement until the microcatheter is at or adjacent to the aneurysm sac. In the illustrated embodiment, the distal end of the second elongate shaft 108 extends within the aneurysm sac, however in other embodiments the distal end of the second elongate shaft 108 can be positioned at the neck of the aneurysm or proximal to the neck of the aneurysm.

In the position shown in FIG. 5A, the system 400 has been advanced within the elongate shaft 108 such that the occlusive member 102 remains in a constrained, low-profile configuration within the shaft 108 while at least a portion of the conduit 452 extends adjacent to the occlusive member 102 and within the shaft 108. In various embodiments, the shaft 108 can have an inner diameter of about 0.017 inches or less, about 0.021 inches or less, or about 0.027 inches or less.

As shown in FIG. 5B, once the distal opening 456 of the conduit 452 is positioned at or near the treatment site (e.g., within the aneurysm sac), the elongate shaft 108 can be retracted, thereby deploying the occlusive member 102 within the aneurysm sac (e.g., allowing the occlusive member 102 to self-expand). Prior to, concurrently with, or after deployment of the occlusive member 102, the stylet 464 may be removed from within the lumen 454 of the conduit 452. With the stylet 464 removed and the occlusive member 102 expanded, the distal portion of the conduit 452 can assume a curved shape, for example curving along an inner wall of the aneurysm sac and/or along an outer surface of the occlusive member 102. In the illustrated embodiment, the distal opening of the conduit 452 is positioned at a distal-most portion of the aneurysm sac, at the dome of the sac.

In this position, the embolic element 230 can be advanced through the conduit 452 and into the aneurysm to a region distal to the occlusive member 102. In the case of a fluid or gel, a syringe or other injector may be used to urge the embolic element 230 through the lumen 454. In the case of microcoils or other structural embolic element(s), a delivery wire or other suitable mechanism may be slidably advanced through the lumen 454 of the conduit 452 to position the embolic element 230 into the aneurysm sac.

As described previously with respect to FIGS. 3A-3G, introduction of the embolic element 230 can cause the occlusive member 102 to deform, for example to at least partially fold in on itself to provide for increased protection in a neck region of the aneurysm. Once the embolic element 230 been delivered and the occlusive member 102 has deformed, the occlusive member 102 can be severed from the core wire 412 as described above. For example, a power supply or other current source can be used to generate current through the core wire 412, resulting in electrolytic corrosion of the core wire 412 at the detachment zone 418.

As shown in FIG. 5C, after the occlusive member 102 is severed via electrolytic corrosion of the detachment zone 418, the core wire 412 and the embolic element delivery assembly 450 can be proximally retracted while the occlusive member 102 and the embolic element 230 remain positioned within the aneurysm. As the embolic element delivery assembly 450 is retracted, the distal portion of the conduit 452 can slide around the expanded occlusive member 102 and out the neck of the aneurysm.

Figure 6:
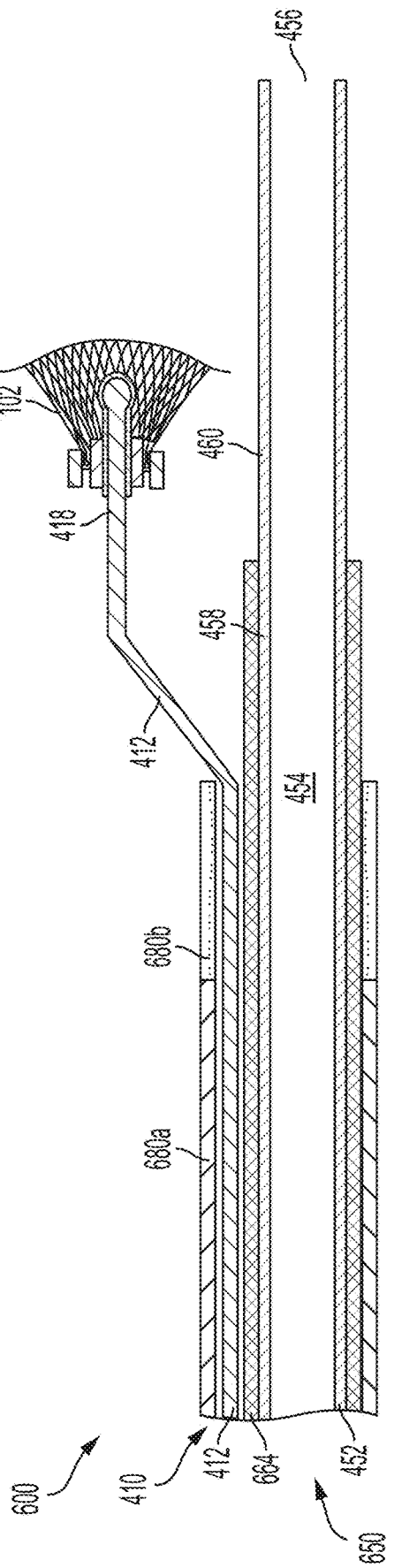
FIG. 6 shows a schematic side view of another embodiment of a treatment system in accordance with aspects of the present technology.

FIG. 6 shows a schematic side view of another embodiment of a treatment system 600 in accordance with aspects of the present technology. The treatment system 600 can include several features that are generally similar to those of FIGS. 4A and 4B described above. For example, an occlusive member delivery assembly 410 includes a core wire 412 having a detachment zone 418 positioned proximal to a hub 424 of the occlusive member 102. The core wire 412 can be coated with an insulative material along some or all of its length (with at least the detachment zone 418 being uncovered by the insulative material).

The core wire 412 runs generally parallel and adjacent to an embolic element delivery assembly 650. This assembly 650 can include several features similar to those described above with respect to FIGS. 4A and 4B, for example having a conduit 452 defining a lumen 454 extending therethrough. In the illustrated embodiment, the conduit 452 can take the form of an extruded polymeric tube (e.g., PTFE) or other suitable material. The conduit 452 can be sufficiently lubricious to facilitate slidable advancement of embolic element(s) therethrough. The conduit 452 can include a proximal portion 458 and a distal portion 460. In the illustrated embodiment, the conduit 452 has a substantially uniform diameter or cross-sectional dimension along its length, and the lumen 454 likewise has a substantially uniform diameter or cross-sectional dimension along its length. In some embodiments, the cross-sectional dimensions of the lumen 454 or the outer surface of the conduit 452 may vary along their lengths.

In contrast to the stylet 464 of FIG. 4A, the system 600 shown in FIG. 6 relies on a surrounding reinforcement member 664 that surrounds at least the proximal portion 458 of the conduit 452. The reinforcement member 664 can be, for example a hypotube, catheter, or other suitable tubular member having sufficient rigidity, hoop strength, and/or other structural characteristics to allow pushability of the assembly 650 through a surrounding delivery catheter without the need for a stylet. Because the distal portion 460 of the conduit 452 is not surrounded by the reinforcement member 664, the distal portion 460 can be more flexible than other portions of the assembly 650. This can facilitate positioning the distal opening 456 of the conduit 452 at the treatment site (e.g., as shown in FIG. 5B). In some embodiments, the reinforcement member 664 can extend substantially the entire length of the conduit 452.

As shown in FIG. 6, the core wire 412 of the occlusive member delivery assembly 410 is coupled together to the embolic element delivery assembly via first and second couplers 680a and 680b. In contrast to the discrete bands illustrated in FIG. 4A, the first coupler 680a shown in FIG. 6 can take the form of an elongated sleeve that circumferentially surrounds both the reinforcement member 664 and the core wire 412 along at least a portion of their respective lengths. The first coupler 680a can be, for example, a tightly fitting polymeric sheath, for example PTFE that has been heat-shrunk into position over the reinforcement member 664 and the core wire 412. Distal to the first coupler 680a is the second coupler 680b, which can take the form of another elongate sleeve circumferentially surrounding the reinforcement member 664 and the core wire 412. The second coupler 680b can be a more flexible polymeric or other suitable material, for example polyether block amide (PEBA), a thermoplastic polyurethane (PTU), or any other suitable material. The more flexible second coupler 680b may serve to better tolerate relative movement of the portion of the core wire 412 that extends away from the reinforcement member 664, as the movement of the core wire 412 can exert an outward force on the second coupler 680b. This can be particularly useful during a resheathing procedure, in which a partially or fully deployed occlusion member 102 is retracted back into a surrounding catheter, which can exert relatively high forces on the core wire 412 and the second coupler 680b. In some embodiments, the two couplers 680a and 680b can be replaced with a single coupler made of any suitable material, or additional couplers may be used.

Although the embodiment of FIG. 6 illustrates the core wire 412 as extending proximally along an outer surface of the reinforcement member 664, in some embodiments, a proximal portion of the core wire 412 can be replaced by or integrated into the reinforcement member 664. For example, in the case of a hypotube as the reinforcement member 664, the hypotube can be configured to carry electrical current along its length to a distally coupled core wire 412 that extends away from the hypotube and is coupled to the occlusive member 102. In another embodiment, the reinforcement member 664 can include a braided catheter, and electrical current may be carried by one or more conductors extending within the wall of the catheter and in electrical communication with the core wire 412.

The system 600 shown in FIG. 6 can be used similar to the method illustrated in FIGS. 5A-5C, except that the system 600 does not include a stylet to be removed after initial positioning of the distal opening 456 of the conduit 452 at the treatment site. As such, the system 600 can be advanced through the vasculature until the occlusive member 102 and the distal opening 456 of the conduit 452 are disposed at or near the treatment site (e.g., within an aneurysm sac). The occlusive member 102 can be deployed (e.g., by retracting a surrounding elongate member 108 to allow the occlusive member 102 to self-expand) and the embolic element 230 may be conveyed through the lumen 454 of the conduit and to the treatment site. Following deployment of the occlusive member 102 and delivery of the embolic element 230, the occlusive member 102 can be electrolytically detached from the core wire 412, and the system 600 can be proximally retracted, leaving the occlusive member 102 and embolic element 230 in position within the aneurysm or other treatment site.

IV. CONCLUSION

Although many of the embodiments are described above with respect to systems and methods related to treatment of hemorrhagic stroke, the technology is applicable to other applications and/or other approaches. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1A-6.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Unless otherwise indicated, all numbers expressing dimensions, percentages, or other numerical values used in the specification and claims, are to be understood as being modified in all instances by the term "about." Accordingly, unless indicated to the contrary, the numerical parameters set forth in the specification and attached claims are approximations that may vary depending upon the desired properties sought to be obtained by the present technology. At the very least, and not as an attempt to limit the application of the doctrine of equivalents to the scope of the claims, each numerical parameter should at least be construed in light of the number of reported significant digits and by applying ordinary rounding techniques. Additionally, all ranges disclosed herein are to be understood to encompass any and all subranges subsumed therein. For example, a range of "1 to 10" includes any and all subranges between (and including) the minimum value of 1 and the maximum value of 10, i.e., any and all subranges having a minimum value of equal to or greater than 1 and a maximum value of equal to or less than 10, e.g., 5.5 to 10.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

The invention claimed is:

1. A treatment system comprising:
an electrolytically corrodible core member having a proximal portion, a distal portion, and a detachment zone between the proximal portion and the distal portion;
an occlusive member having a proximal hub coupled to the core member distal portion, the occlusive member having: (1) a constrained state for delivery to an aneurysm; (2) a first expanded state in which at least a portion of the occlusive member is configured to be disposed across a neck of the aneurysm, and (3) a second expanded state in which an embolic element disposed between a distal face of the occlusive member and a wall of the aneurysm causes a sidewall of a portion of the occlusive member to invert such that the portion of the occlusive member is convex towards the aneurysm wall in the first expanded state and concave towards the aneurysm wall in the second expanded state; and
a conduit extending along at least a portion of the core member, the conduit having a distal portion configured to be disposed within the aneurysm along with the occlusive member, the conduit having a lumen configured to pass the embolic element therethrough.

2. The treatment system of claim 1, wherein the conduit comprises a flexible tubular member.

3. The treatment system of claim 1, wherein the conduit comprises a hypotube.

4. The treatment system of claim 1, wherein the core member comprises an elongated tubular member.

5. The treatment system of claim 1, wherein the conduit distal end extends to or distal to a distal end of the occlusive member.

6. The treatment system of claim 1, wherein the core member comprises a proximal insulating layer annularly contacting the proximal portion of the core member and a distal insulating layer annularly contacting the distal portion of the core member.

7. The treatment system of claim 1, wherein the embolic element is a liquid embolic.

8. A treatment system comprising:
a core member having a proximal portion, a distal portion, and a detachment zone between the proximal portion and the distal portion;
an occlusive member having a proximal hub coupled to the core member distal portion, the occlusive member having a constrained state for delivery to an aneurysm and an expanded state in which at least a portion of the occlusive member is configured to be disposed across a neck of the aneurysm while an embolic element is disposed between a distal face of the occlusive member and a wall of the aneurysm, wherein the occlusive member has a first internal volume in the expanded state in which a portion of the occlusive member is convex towards a wall of the aneurysm and the occlusive member is configured to at least partially collapse when contacted by the embolic element, thereby reducing the internal volume from the first internal volume to a second internal volume in which the portion of the occlusive member is concave towards the aneurysm wall; and
a conduit lumen extending along at least a portion of the core member and configured to pass the embolic element therethrough to within the aneurysm, the conduit lumen having a distal end configured to be disposed within the aneurysm concurrently with the occlusive member.

9. The treatment system of claim 8, wherein the conduit lumen is defined by a conduit extending alongside at least a portion of the core member, the conduit having a distal end configured to extend distal to a distal end of the occlusive member.

10. The treatment system of claim 8, wherein the detachment zone comprises a portion of the core member configured to be severed via electrolytic corrosion.

11. The treatment system of claim 8, wherein the core member comprises an elongate tubular shaft.

12. The treatment system of claim 11, wherein the conduit lumen extends through the elongate tubular shaft.

13. The treatment system of claim 8, wherein the conduit lumen is configured to pass the embolic element through the core member.

14. The treatment system of claim 8, wherein the embolic element is a liquid embolic.

15. A treatment system comprising:
an elongate tubular member having a proximal portion, a distal portion, and a detachment zone between the proximal portion and the distal portion;
an occlusive member having a proximal hub coupled to the tubular member distal portion, the occlusive member having a constrained state for delivery to an aneurysm and an expanded state in which at least a portion of the occlusive member is configured to be disposed across a neck of the aneurysm while an embolic element is disposed between a distal face of the occlusive member and a wall of the aneurysm, wherein the occlusive member has a first internal volume in the expanded state in which a portion of the occlusive member is convex towards a wall of the aneurysm and the occlusive member is configured to at least partially collapse when contacted by the embolic element, thereby reducing the internal volume from the first internal volume to a second internal volume in which the portion of the occlusive member is concave towards the aneurysm wall; and a conduit extending through the elongate tubular member and defining a conduit lumen configured to pass the embolic element therethrough to within the aneurysm, the conduit lumen having a distal end configured to be in fluid communication with the aneurysm while the occlusive member is disposed within the aneurysm.

16. The treatment system of claim 15, wherein the detachment zone comprises a portion of the tubular member configured to be severed via electrolytic corrosion.

17. The treatment system of claim 15, wherein the conduit comprises a flexible tubular member.

18. The treatment system of claim 15, wherein the conduit comprises a hypotube.

19. The treatment system of claim 15, wherein the conduit distal end extends to a distal end of the occlusive member.

20. The treatment system of claim 15, wherein the embolic element is a liquid embolic.

\* \* \* \* \*